US005519008A

United States Patent [19]
Rao et al.

[11] Patent Number: 5,519,008
[45] Date of Patent: May 21, 1996

[54] DERIVATIVES OF TRITERPENOID ACIDS AS INHIBITORS OF CELL-ADHESION MOLECULES ELAM-1 (E-SELECTIN) AND LECAM-1 (L-SELECTIN)

[75] Inventors: Narasinga Rao, Alameda; Mark B. Anderson, Orinda, both of Calif.; John J. Naleway, Eugene, Oreg.; John H. Musser, San Carlos, Calif.

[73] Assignee: Glycomed Incorporated, Alameda, Calif.

[21] Appl. No.: 943,356

[22] Filed: Sep. 10, 1992

[51] Int. Cl.$^6$ .......................... A01N 37/00; A01N 39/00; A61K 31/00; A61K 31/56

[52] U.S. Cl. ................... 514/26; 514/2; 514/25; 514/53; 514/54; 514/61; 514/563; 536/5; 536/17.2; 536/17.3; 536/17.4; 536/17.5; 536/17.6; 536/18.1; 536/22.1; 536/55; 536/55.1; 552/502

[58] Field of Search .................. 536/55, 55.1, 17.2–17.6, 536/18.1, 22.1, 5; 552/502; 514/53, 54, 61

[56] References Cited

U.S. PATENT DOCUMENTS

| | | | |
|---|---|---|---|
| 4,084,010 | 4/1978 | Takemoto et al. | 426/548 |
| 4,568,665 | 2/1986 | Mitchell | 514/9 |
| 4,987,125 | 1/1991 | Han et al. | 514/33 |
| 5,019,495 | 5/1991 | Shanbrom | 435/1 |
| 5,204,324 | 4/1993 | Shanbrom | 514/2 |

FOREIGN PATENT DOCUMENTS

| | | |
|---|---|---|
| 503582A1 | 9/1992 | European Pat. Off. . |
| 3429590A1 | 10/1984 | Germany . |
| 6038392 | 8/1983 | Japan . |
| 1301642 | 5/1988 | Japan . |
| 89-226822A | 9/1989 | Japan . |
| 4190799 | 11/1990 | Japan . |
| 1625882A1 | 2/1991 | U.S.S.R. . |
| 2140809 | 12/1984 | United Kingdom . |

OTHER PUBLICATIONS 60-178898—Japan—no translation.
63-243093—Japan—no translation.
61-148142—Japan—no translation.
62-51604—Japan—nop translation.
4-190799—Japan—no translation.
3-271239—Japan—no translation.
Acta Pharmaceutica Sinica 1988; 23(7):553–560—no translation.
Baran, J. S. et al. (1974) J. Med. Chem. 17:2, 184–191.
Brieskorn, C. H. et al. (1970) Arch. der Pharmazie, 11:905–919.
Marsh, C. A., et al. (1956) J. Biochem. 63:9–14.
Lythogoe, B. et al. (1950) J. Chem. Society 63:1983–1991.
Louis, L. H. et al. (1956) J. Lab. Clin. Med. 47–1:20–28.
Ruzieka, L. et al. (1936) Helv. Chim. Acta. 19:1402–1406—no translation.
Karrer, P. et al. (1921) Helv. Chim. Acta. 4:100–113—no translation.
Soviet Union Issued Patent—SU1499–902–A; issued May 7, 1991—abstract only.
Soviet Union Issued Patent—SU1513–882–A; issued May 7, 1991—abstract only.
Ying, et al., "Inhibition of human leucocyte elastase by ursolic acid," Biochem. J. (1991) vol. 277, 521–526.
Taylor, "Bacterial Triterpenoids," Microb. Reviews., vol. 48, No. 3 (Sep. 1984) pp. 181–198.
Narasinga, B. N., et al., "Sialyl Lewis X Mimics Derived from a Pharmacore Search Are Selectin Inhibitors with Anti–Inflammatory Activity", *J. Biol. Chemistry*, 269:19663–19666 (1994).
Harlan, John M., et al., "In Vivo Models of Leukocyte Adherence to Endothelium", Ch. 6, 117–150 in *Adhesion: Its Role in Inflammatory Response* (1992).
Saitoh, Osamu, et al., "Differential Glycosylation and Cell Surface Expression of Lysosomal Membrane Glycoproteins in Sublines of a Human Colon Cancer Exhibiting Distinct Metastatic Potentials", *J. Biol. Chemistry*, 267:5700–5707 (1992).
Wattenberg, Lee, et al., "Cancer Chemoprevention", pp. 25–39 (1992).
Wattenberg, Lee, et al., "Cancer Chemoprevention", pp. 51–56 (1992).
Nishino, Hoyoku, "Antitumor–Promoting Activity of Glycyrrhetinic Acid and Its Related Compounds", *Cancer Chemoprevention*, pp. 457–467 (1992).
CA: 116: 40103f (1992) Nakamura.
CA 113: 103375g Kitagawa (1990).
CA 121(19): 231262v Saito (1994).
CA 115(2): 153673r Aquino (1991).
CA 113(2): 12139s Zen (1990).
J. Cell. Biol. 119(1) Erbe et al. (1992).
JACS 115, 7549–7550, De Frees (1993).

*Primary Examiner*—Douglas W. Robinson
*Assistant Examiner*—James Oliver Wilson
*Attorney, Agent, or Firm*—Lyon & Lyon

[57] ABSTRACT

Triterpenoid acid derivatives have been found to have structures similar to natural ligands to the extent that these derivatives bind to natural selectin receptors including endothelial leukocyte adhesion molecule-1 (ELAM-1) and leukocyte/endothelial cell adhesion molecule-1 (LECAM-1). The molecules can be administered to the patients by themselves or in pharmaceutical formulations; in order to alleviate inflammation and/or treat other abnormalities associated with the excessive binding of leukocytes to endothelial receptors.

7 Claims, 2 Drawing Sheets

DERIVATIVES OF TRITERPENOID ACIDS AS INHIBITORS OF CELL-ADHESION MOLECULES ELAM-1 (E-SELECTIN) AND LECAM-1 (L-SELECTIN)

FIELD OF THE INVENTION

This invention relates generally to the field of chemical compounds, and to methods of treatment and detection. More specifically, this invention relates to derivatives of triterpenoid acids, formulations containing such and their use in treating patients by binding to and/or blocking cellular receptors and thereby alleviating a variety of symptoms including inflammation.

BACKGROUND OF THE INVENTION

The successful function of many systems within multicellular organisms are dependent on cell-cell interactions. Such interactions are affected by the alignment of particular ligands with particular receptors in a manner which allows for ligand-receptor binding and thus a cell-cell adhesion. While protein-protein interactions in cell recognition have been recognized for some time, only recently has the role of carbohydrates in physiologically relevant recognition been widely considered (see Brandley, B. K., and Schnaar, R. L., *J. Leuk. Biol.* (1986) 40:97; and Sharon, N., and Lis, H., *Science* (1989) 246:227). Oligosaccharides are well positioned to act as recognition molecules due to their cell surface location and structural diversity. Many oligosaccharide structures can be created through the differential activities of a smaller number of glycosyltransferases. Their diverse structures, then, can be generated by transcription of relatively few gene products, suggesting a plausible mechanism for establishing the information necessary to direct a wide range of cell-cell interactions. Examples of differential expression of cell surface carbohydrates and putative carbohydrate binding proteins (lectins) on interacting cells have been described (see Dodd, J., and Jessel, T. M., *J. Neurosci.* (1985) 5:3278; Regan, L. J., et al., *Proc. Natl. Acad. Sci. USA* (1986) 83:2248; Constantine-Paton, M., et al., *Nature* (1986) 324:459; and Tiemeyer, M., et al., *J. Biol. Chem.* (1989) 263:1671).

A large body of data has been accumulated that implicates a family of receptors, the selectins (or Lectin, EGF, Complement-Cellular Adhesion Molecules) (hereinafter LECCAMs) in many of the initial interactions between leukocytes and vascular endothelia. The three known members of this family, L-Selectin (LECAM-1, LAM-1, gp90MEL), E-Selectin (LECAM-2, ELAM-1) and P-Selectin (LECAM-3, GMP-140, PADGEM), each contain a domain with homology to the calcium-dependent lectins (C-lectins), an EGF-like domain, and several complement binding protein-like domains (Bevilacqua et al., *Science* (1989) 243:1160–1165; Johnston et al., *Cell* (1989) 56:1033–1044; Lasky et al., *Cell* (1989) 56:1045–1055; Tedder et al., *J. Exp. Med.* (1989) 170:123–133).

Identification of the C-lectin domains has led to an intense effort to define carbohydrate ligands for these proteins. There is now general agreement that E-selectin recognizes the carbohydrate sequence NeuNAcα2-3Galβ1-4(Fucα1-3)GlcNAc (sialyl-Lewis x, or sLe$^x$) and related oligosaccharides (Berg et al., *J. Biol. Chem.* (1991) 265:14869–14872; Lowe et al, *Cell* (1990) 63:475–484; Phillips et al., *Science* (1990) 250:1130–1132; Tiemeyer et al., *Proc. Natl. Acad. Sci. USA* (1991) 88:1138–1142; Tyrrell, *Proc. Natl. Acad. Sci. USA*, in press). P-Selectin has been reported to recognize the Lewis x structure (Galβ1-4(Fucα1-3) GlcNAc) (Larsen et al., *Cell* (1990) 63:467–474). Others report that an additional terminal linked sialic acid is required for high affinity binding (Moore et al., *J. Cell. Biol.* (1991) 112:491–499). Recently Polley et al., *Proc. Natl. Acad. Sci. USA* (1991) 88:6224–6228, have described experiments suggesting that such a structure (sLe$^x$) is also a ligand for P-Selectin, although there is disagreement on this point.

The carbohydrate ligand for perhaps the most widely studied selectin, L-Selectin, has been extremely difficult to define. This is primarily due to the relative difficulty in obtaining significant quantities of high endothelial venules, the tissue thought to contain most of the native ligand. Data (Imai et al., *J. Cell Biol.* (1991) 113:1213–1221; Stoolman & Rosen, *J. Cell Biol.* (1983) 96:722–729; True et al., *J. Cell Biol.* (1990) 111:2757–2764; Yednock et al., *J. Cell Biol.* (1987) 104:713–723) suggest the L-Selectin ligand may contain fucose, mannose and/or sialic acid, with possible additional anionic components provided by sulfate or phosphate esters. Recently, glycoprotein ligands of L-Selectin have been isolated from mouse HEV (Imai et al., 1991). These glycoproteins possess many of the residues expected for a native ligand (fucose, sialic acid, sulfate), although neither the structure of the carbohydrate chains nor the exact nature of the residues required for recognition have been defined as yet.

Tumor-associated glycolipids have been reported in fetal tissue and a variety of human cancers, including CML cells (Fukuda, M. N., et al., *J. Biol. Chem.* (1986) 261:2376; Magnani, J. L., et al., *J. Biol. Chem.* (1982) 257:14365; Hakomori, S., et al., *Biochem. Biophys. Res. Comm.* (1983) 113:791). This has led to the hypothesis that these structures may be important in many developmental and oncogenic processes (Magnani, J. L., et al., *J. Biol. Chem.* (1982) 257:14365). Smaller quantities of most of these carbohydrates can be found in normal human tissue (see Fukushi, Y., et al., *J. Exp. Med.* (1984) 160:506), but until now no function for these structures has been reported.

Adhesion of circulating neutrophils to stimulated vascular endothelium is a primary event of the inflammatory response.

LECAM-1 is particularly interesting because of its ability to block neutrophil influx (Watson et al., *Nature* (1991) 349:164–167). It is expressed in chronic lymphocytic leukemia cells which bind to HEV (see Spertini et al., *Nature* (1991) 349:691–694). It is also believed that HEV structures at sites of chronic inflammation are associated with the symptoms of diseases such as rheumatoid arthritis, psoriasis, and multiple sclerosis.

The present inventors have now found that selectins recognize derivatives of triterpenoid acids which can inhibit binding between leukocytes and endothelial cells and, as a consequence of that discovery, have developed the present invention.

SUMMARY OF THE INVENTION

Ligand molecules of the invention are in the form of derivatives of triterpenoid acids. These molecules are capable of binding to and interrupting the biological chain of events associated with selectins. The ligand molecules act as biochemical blocking agents by binding to the selectin receptors (LECAM-1 on circulating leukocytes and/or ELAM-1 on endothelial cells), thereby preventing the leukocytes from binding to endothelial cells. This blocking prevents or alleviates a primary event of the inflammatory response.

The ligands can be labeled, bound to pharmaceutically active drugs such as anti-neoplastic agents and anti-inflammatory drugs and/or formulated to provide: (1) compositions useful in assaying a sample for the presence of a selectin, (2) compositions useful in detecting the presence of leukocytes and/or endothelial cells in a sample, (3) pharmaceutical compositions useful in treating conditions associated with the excessive migration of leukocytes from the circulatory system, and/or (4) blocking other effects involving the interaction of circulating leukocytes with other tissue.

An important aspect of the invention is pharmaceutical compositions which are useful in treating, preventing and/or alleviating any undesirable effects resulting from the excessive migration of circulating leukocytes into surrounding tissues. Such compositions are comprised of an inactive ingredient in the form of a pharmaceutically acceptable excipient material and a compound capable of binding to a selectin receptor, in particular a compound having the following general structural formula (I):

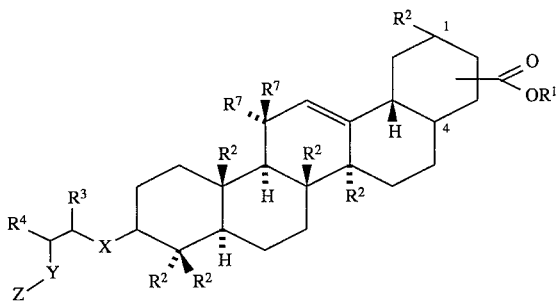

wherein:
$R^1$ is H or lower alkyl containing 1 to 4 carbon atoms;

$R^2$ is $CH_2OR^1$ or $CH_3$;

$R^3$ and $R^4$ are each independently H or alkyl containing 1 to 6 carbon atoms or $R^3$ and $R^4$, taken together, form a deoxy sugar in its D or L form or a six-membered ring optionally containing a heteroatom selected from the group consisting of O, S, $NR^1$, wherein said six-membered ring may further be substituted by one or more substituents selected from the group consisting of $CH_2OR^1$, $OR^1$, $OOCR^1$, $NR^1$, $NHCOR^1$, $SR^1$, $COOR^1$;

X is O, S, $NR^1$;

Y is O, S, $NR^1$; and

Z is $CHR^5(CHOR^1)_n CHR^6$ or an aromatic ring substituted with up to 3-OH, wherein $R^5$ and $R^6$ are each independently H, lower alkyl or taken together to form a five or six-membered ring optionally containing a heteroatom selected from the group of O, S, and $NR^1$;

said five or six-membered ring optionally substituted with a substituent selected from group consisting of $CH_2OR^1$, $OR^1$, $OOCR^1$, $NR_2$, $NHCOR^1$ and $SR^1$;

with the proviso that if $R^3$ and $R^4$, taken together, provide a hexose substituent, Z cannot represent a hexose substituent;

n is 2 or 3

$R^7$ is $H_2$ or O, $NR^1$ with the proviso that if E ring substitution is in the 1-position, $R^3$ and $R^4$ taken together cannot provide a hexose substituent.

The structure of formula I above may be in different isomeric forms and such are encompassed by this disclosure.

In particular the moiety at the $R^3$ position may be in either the alpha or beta configuration and the linkage by which any sugar is attached at the $R^3$ position may be either axial or equatorial. However, here and throughout the different stereo configurations are not shown but are understood to be encompassed by this disclosure and the appended claims.

A primary object of the invention is to provide selectin ligands in the form of derivatives of triterpenoid acids.

Another object of the invention is to provide a selectin ligand in a useful formulation, preferably a pharmaceutical formulation.

Another object is to provide a composition comprising a selectin ligand which is preferably labeled and which can be used to assay for the presence of a selectin such as ELAM-1 and/or LECAM-1 in a sample.

Another object is to provide a pharmaceutical formulation containing a selectin ligand which is useful in treating inflammation.

Other objects include providing methods to treat inflammation and to determine the site of inflammation by administering formulations of the type referred to above.

An advantage of the invention is that the ligands are in the form of non-toxic derivatives of triterpenoid acids with particular functional groups and three-dimensional configurations which allow them to effectively bind selectin receptors and thereby block neutrophils from binding to endothelial cells in effective numbers per unit of time which result in inflammation and/or other adverse effects.

A feature of the present invention is that the ligands can be labeled and the labeled ligand used in an assay to detect the presence of LECAM-1 or ELAM-1 in a sample.

Other features of the invention include the ability of pharmaceutical formulations of the invention to relieve the inflammatory symptoms of a wide range of diseases which are characterized by the binding of excessive amounts of neutrophils to a tissue site, i.e., a site which possesses the ELAM-1 receptor.

These and other objects, advantages and features of the present invention will become apparent to those persons skilled in the art upon reading the details of the isolation, structure, formulation and usage as more fully set forth below, references being made to the accompanying figures and general structural formulae forming a part hereof wherein like symbols refer to like molecular moieties throughout.

BRIEF DESCRIPTION OF THE DRAWINGS

This invention may be better understood and its numerous objects, advantages and features will become apparent to those skilled in the art by reference to the accompanying drawings as follows.

DETAILED DESCRIPTION OF PREFERRED EMBODIMENTS

Before the present selectin ligands and composition containing such ligands and processes for isolating and using such are described, it is to be understood that this invention is not limited to the particular compositions, methods or processes described as such compositions and methods may, of course, vary. It is also to be understood that the terminology used herein is for the purpose of describing particular embodiments only, and is not intended to be limiting since the scope of the present invention will be limited only by the appended claims.

It must be noted that as used in this specification and the appended claims, the singular forms "a", "an" and "the" include plural referents unless the context clearly dictates otherwise. Thus, for example, reference to "a ligand" includes mixtures of ligands, reference to "an ELAM-1" includes reference to mixtures of such molecules, reference to "the formulation" or "the method" includes one or more formulations, methods and/or steps of the type described herein and/or which will become apparent to those persons skilled in the art upon reading this disclosure and so forth.

Unless defined otherwise all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described herein. All publications mentioned herein are incorporated herein by reference.

Some standard abbreviations used in connection with the present invention include: BSA, bovine serum albumin; DEAE, diethylaminoethyl; DMSO, dimethylsulfoxide; ELAM-1, endothelial/leukocyte adhesion molecule-1; HPTLC, high performance thin layer chromatography; LECAM-1, leukocyte/endothelial cell adhesion molecule-1; MOPS, 3-[N-Morpholino]propanesulfonic acid; NANA, N-acetylneuraminic acid; PVC, polyvinylchloride; TLC, thin layer chromatography; TFA, trifluoroacetic acid; Tris, tris (hydroxymethyl) aminomethane.

A. General Overview

Figure 1:
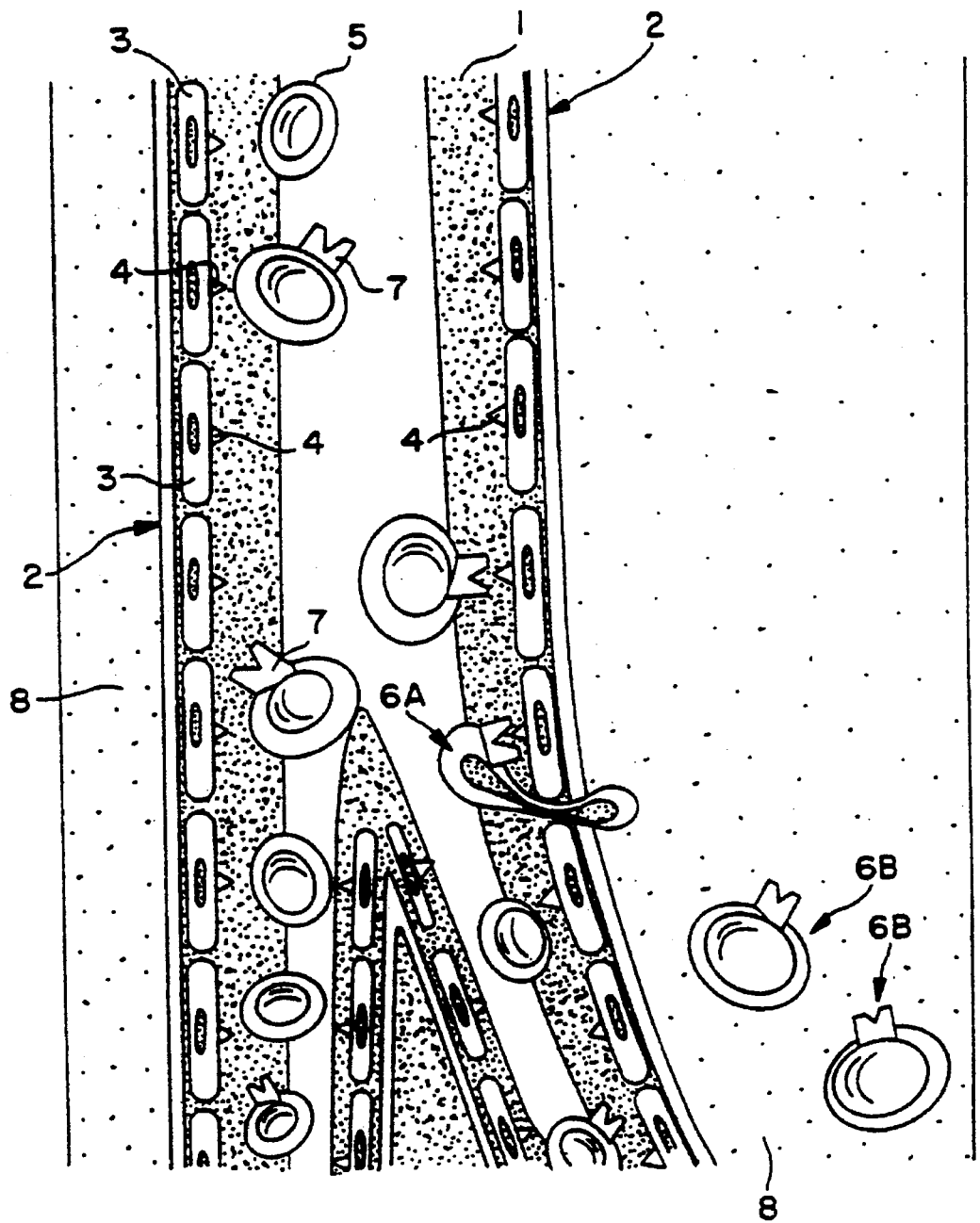
FIG. 1 is a cross-sectional schematic view showing the interaction between white blood cells and activated endothelial cells.

Referring now to FIG. 1, a cross-sectional view of a blood vessel 1 is shown. The vessel wall 2 is lined internally with endothelial cells 3. The endothelial cells 3 can be activated causing the cells 3 to synthesize ELAM-1 which is displayed in FIG. 2 as a triangular surface receptor 4. Both red blood cells 5 and white blood cells 6 flow in the vessel 1. The white blood cells 6 display carbohydrate ligands 7 which have chemical and physical characteristics which allow the ligands 7 to bind to the receptors 4. Once the ligand 7 binds to the receptor 4, the white blood cell 6 is brought through the vessel wall 2 as is shown with the white blood cell 6A. The white blood cells 6B brought into the surrounding tissue 8 can have positive effects, such as fighting infection, and negative effects, such as inflammation.

Figure 2:
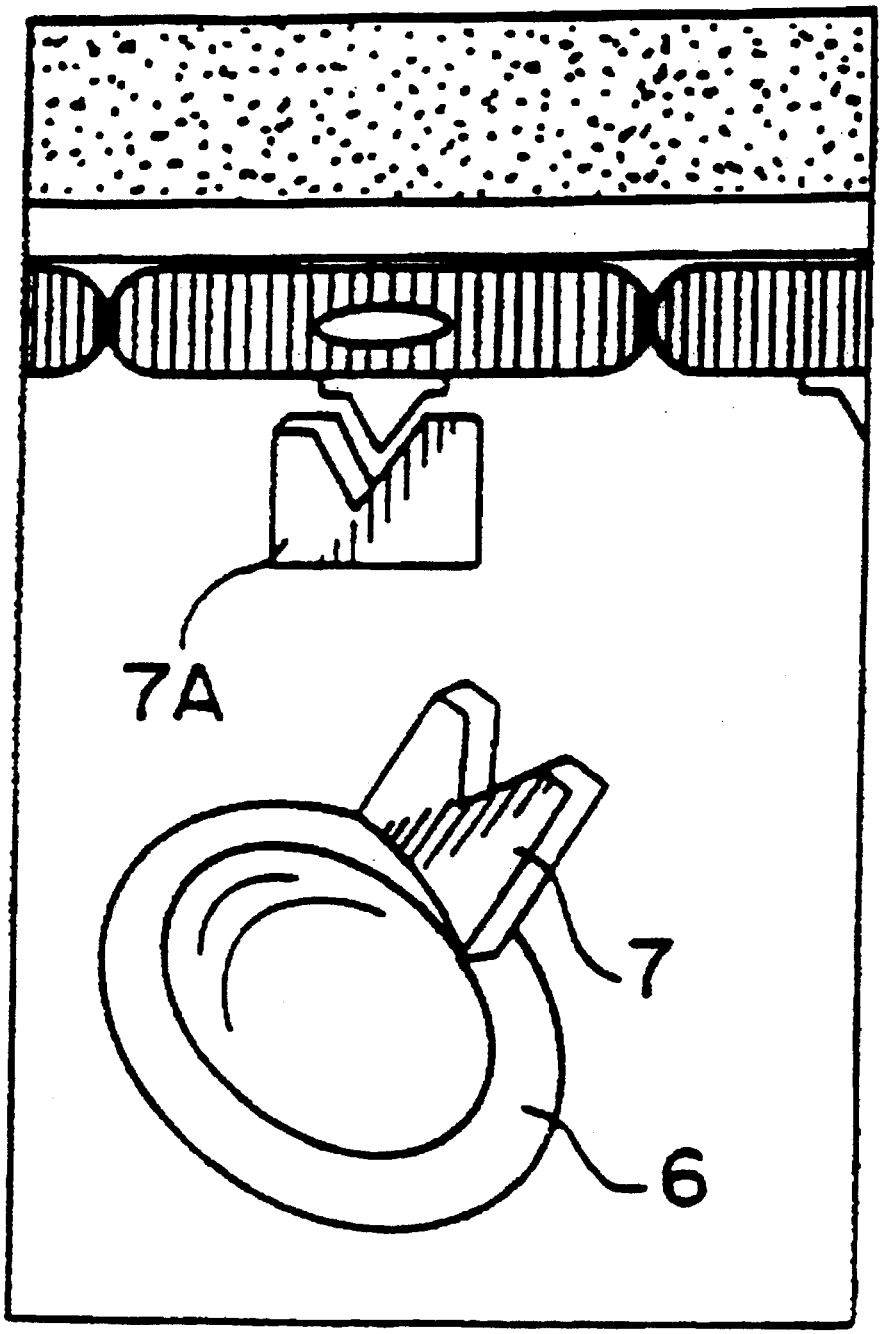
FIG. 2 is a cross-sectional schematic view showing how ligands of the invention might be used as pharmaceuticals to block ELAM-1.

An important aspect of the present invention can be described by referring to FIG. 2. The present inventors have produced ligands 7 apart from their presence on the surface of white blood cells 6. These isolated ligands 7A adhere to ELAM-1 by themselves and can be formulated into pharmaceutical compositions, which when administered will effectively block the ELAM-1 and prevent the adhesion of a receptor 7 connected to a white blood cell 6. By administering pharmaceutically effective amounts of ligands 7A, some, but not all, of the white blood cells will not reach the surrounding tissue 8. By slowing the rate at which the white blood cells reach the surrounding tissue, inflammation can be prevented and/or alleviated.

It is known that for an acute inflammatory response to occur, circulating neutrophils must bind to and penetrate the vascular wall and access the site of injury. Several molecules have been implicated in this interaction, including a family of putative carbohydrate ligands and their receptors. One molecule which has been previously isolated and identified is the endogenous carbohydrate ligand for endothelial leukocyte adhesion molecule-1 (hereinafter ELAM-1) and the ligand for LECAM-1. The present invention involves the characterization and synthesis of such ligand molecules which are derivatives of triterpenoid acids and bind to both ELAM-1 and LECAM-1.

For certain cancers to spread cell-cell adhesion must take place. This adhesion can be interrupted by the administration of compounds of the invention which generally aid in blocking cell-cell adhesion. Accordingly, compounds of the invention can be used to retard the spread of cancer cells which display receptors which adhere to a compound of formula I.

Testing Triterpenoid Acid Derivatives Their Ability to Act as Ligands

Derivatives of triterpenoid acids encompassed by general structural formula (I) can be tested in accordance with an assay procedure in order to determine if these derivatives act as ligands and therefore would be encompassed by the present invention and be useful in producing pharmaceutical compositions which could be used in various treatments such as treatments to alleviate inflammation. Such assays involve the use of radio labeled COS cells which express cell surface receptors such as cell surface ELAM-1 receptors. These cells are used as probes to screen compounds by determining if the compounds adhere to these cells under assay conditions known to those skilled in the art.

After appropriate compounds are identified the compounds can be formulated by combining the compounds with pharmaceutically acceptable excipient materials and administering the pharmaceutical composition to the patient such as by intravenous injection in an amount sufficient to alleviate inflammation. The details of carrying out the assay in order to identify useful ligands is described below.

Identification of Putative ELAM-1 Ligands Using Recombinantly Produced Receptor

A complete cDNA for the ELAM-1 receptor was obtained by PCR starting with total RNA isolated from IL-1 stimulated human umbilical vein endothelium. The resulting cDNA was inserted into the CDM8 plasmid (see Aruffo, A., and Seed, B., *Proc. Natl. Acad. Sci. USA* (1987) 84:8573) and the plasmid amplified in *E. coli*. Plasmid DNA from individual colonies was isolated and used to transfect COS cells. Positive plasmids were selected by their ability to generate COS cells that support HL-60 cell adhesion. DNA sequencing positively identified one of these clones as encoding for ELAM-1 (Bevilacqua, M. P., et al., *Science*, (1989) 243:1160; Polte, T., et al., *Nucleic Acids Res.* (1990) 18:1083; Hession, C., et al., *Proc. Natl. Acad. Sci. USA* (1990) 87:1673). These publications are incorporated herein by reference for their disclosure of ELAM-1 and genetic material coding for its production. The complete nucleotide sequence of the ELAM-1 cDNA and predicted amino acid sequence of the ELAM-1 protein are given in the above cited article by Bevilacqua et al., which DNA and amino acid sequences are incorporated herein by reference (see also published PCT patent application WO90/13300 which was published Nov. 15, 1990, and which is incorporated herein by reference).

COS cells, expressing membrane-bound ELAM-1, were metabolically radiolabeled with $^{32}PO_4$ and used as probes in two assay systems to screen for recognition of triterpenoid acid derivatives. In the first, triterpenoid acid derivatives were adsorbed to the bottoms of PVC microtiter wells, while in the second they were resolved on TLC plates. In both assays these triterpenoid acid derivatives were probed for their ability to support adhesion of ELAM-transfected COS cells, untransfected COS cells, or COS cells transfected with a plasmid containing an irrelevant cDNA, under conditions of controlled detachment force (see Swank-Hill, P., et al., *Anal. Biochem.* (1987) 183:27; and Blackburn, C. C., et al., *J. Biol. Chem.* (1986) 261:2873 each of which is incorporated herein by reference to disclose the details of such assaying methodology).

Conjugates

It should be pointed out that various "linker" groups can be attached to the triterpenoid acid derivatives of the present invention and the linker groups can be used to attach various additional compounds such as pharmaceutically acceptable drugs. By using the linker various conjugates are formed i.e. ligand-linker-drug conjugates are formed which provide effective drug delivery systems for the drug which is linked to the ligand compound of the invention. It is especially preferred to attach a drug with anti-inflammatory characteristics in that the ligand binds to ELAM-1 which is associated with inflammation. Accordingly, non-steroidal anti-inflammatory drugs (NSAIDs) such as naproxen or ibuprofen which act as anti-inflammatory agents could be administered bound to the ligand and could be administered systemically in smaller amounts than usual while obtaining an equivalent effect or even greater anti-inflammatory effect at the site of inflammation. The drug could be attached by an enzymatically clearable linker cleaved by an enzyme such as an esterase. Any other drugs which might be attached include, but are not limited to, antibiotics, vasodilators and analgesics. Such a drug delivery system would reduce any systemic effect normally caused by the drug in that the drugs could be administered in amounts of one-half to one-tenth the normal dose and still obtain the same anti-inflammatory result at the site of inflammation, without adverse side effects.

USE and ADMINISTRATION

The triterpenoid acid derivatives compounds of the invention can be administered to a subject in need thereof to treat the subject by either prophylactically preventing inflammation or relieving it after it has begun. The ligands are preferably administered with a pharmaceutically acceptable carrier, the nature of the carrier differing with the mode of administration, for example, oral administration, usually using a solid carrier and I.V. administration a liquid salt solution carrier. The formulation of choice can be accomplished using a variety of excipients including, for example, pharmaceutical grades of mannitol, lactose, starch, magnesium stearate, sodium saccharin cellulose, magnesium carbonate, and the like. Oral compositions may be taken in the form of solutions, suspensions, tablets, pills, capsules, sustained release formulations, or powders. Particularly useful is the administration of the subject ligand molecules directly in transdermal formulations with permeation enhancers such as DMSO. Other topical formulations can be administered to treat dermal inflammation.

A sufficient amount of ligand molecules should be administered to bind to a substantial portion of the ELAM-1 expected to cause or actually causing inflammation so that inflammation can either be prevented or ameliorated. Thus, "treating" as used herein shall mean preventing or ameliorating inflammation and/or symptoms associated with inflammation. Typically, the compositions of the instant invention will contain from less than 1% to about 95% of the active ingredient, preferably about 10% to about 50%. Preferably, between about 10 mg and 50 mg will be administered to a child and between about 50 mg and 1000 mg will be administered to an adult. The frequency of administration will be determined by the care given based oil patient responsiveness. Other effective dosages can be readily determined by one of ordinary skill in the art through routine trials establishing dose response curves.

In determining the dose of selectin ligands to be administered, it must be kept in mind that one may not wish to completely block all of the selectin receptors. In order for a normal healing process to proceed, at least some of the white blood cells or neutrophils must be brought into the tissue in the areas where the wound, infection or disease state is occurring. The amount of the selectin ligands administered as blocking agents must be adjusted carefully based on the particular needs of the patient while taking into consideration a variety of factors such as the type of disease that is being treated.

It is believed that the ligands or blocking agents of the present invention can be used to treat a wide range of diseases, including diseases such as rheumatoid arthritis and multiple sclerosis. The compositions of the invention should be applicable to treat any disease state wherein the immune system turns against the body causing the white cells to accumulate in the tissues to the extent that they cause tissue damage, swelling, inflammation and/or pain. The inflammation of rheumatoid arthritis, for example, is created when large numbers of white blood cells quickly enter the joints in the area of disease and attack the surrounding tissues.

Formulations of the present invention might also be administered to prevent the undesirable aftereffects of tissue damage resulting from heart attacks. When a heart attack occurs and the patient has been revived, such as by the application of anticoagulants or thrombolytic (e.g., tPA), the endothelial lining where a clot formed has often suffered damage. When the antithrombotic has removed the clot, the damaged tissue beneath the clot and other damaged tissue in the endothelial lining which has been deprived of oxygen, become activated. The activated endothelial cells then synthesize the ELAM-1 receptors within hours of the cells being damaged. The receptors are extended into the blood vessels where they adhere to glycolipid ligand molecules on the surface of white blood cells. Large numbers of white blood cells are quickly captured and brought into the tissue surrounding the area of activated endothelial cells, resulting in inflammation, swelling and necrosis which thereby decreases the likelihood of survival of the patient.

In addition to treating patients suffering from the trauma resulting from heart attack, patients suffering from actual physical trauma could be treated with formulations of the invention in order to relieve the amount of inflammation and swelling which normally result after an area of the body is subjected to severe trauma. Other disease states which might be treatable using formulations of the invention include various types of arthritis and adult respiratory distress syndrome. After reading the present disclosure, those skilled in the art will recognize other disease states and/or symptoms which might be treated and/or mitigated by the administration of formulations of the present invention.

Other modes of administration will also find use with the subject invention. For instance, the ligand molecules of the invention can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), preferably about 1% to about 2%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject-proteins by the nasal mucosa.

The ligand molecules of the instant invention may also be administered as injectables. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles. The ligands in the form of compounds of formula I can be mixed with compatible, pharmaceutically acceptable excipients.

Suitable vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the ligand molecules adequate to achieve the desired state in the subject being treated.

The various ligand compounds of the present invention can be used by themselves or in combination with pharmaceutically acceptable excipient materials as described above. However, the ligand compounds of the invention can be made as conjugates wherein the compounds of the invention are linked in some manner to a label. By forming such conjugates, the ligand compounds of the invention act as biochemical delivery systems for the label so that a site of inflammation can be detected.

The ligand molecules of the invention could also be used as laboratory probes to test for the presence of a selectin receptor in a sample. Such probes are preferably labeled such as with a radioactive, fluorescent or enzyme activated label.

SYNTHETIC STRATEGY

Synthesis of the various glycyrrhetinic acid conjugates requires manipulation about the 3-position of the triterpene nucleus. Many of these manipulations involve a double inversion methodology about this center. The syntheses of the key 3α-iodo compounds (1b, 4a, 8b and 9b) can be accomplished by a method similar to that used by Greenhouse and Muchowski [Greenhouse, R., Muchowski, J. M., Can. J. Chem. 59 (1981) 1025–1027] for the synthesis of 3-desoxy-3α-iododigitoxigenin. This involves treatment of a 3β-hydroxy derivative with triphenylphosphine iodide. Attempts in the literature to afford such a nucleophilic displacement by the two step procedure of forming the β-O-tosylate, and subsequent displacement with sodium iodide gave preponderantly a 3β-iodo derivative [Bayless, A. V., Zimmer, H., Tet. Lett. 35 (1968) 3811–3812.].

Formation of the various 3β-alkyl ethers is as follows. The use of oxidative solvolytic displacement of a hypervalent iodine compound [Cambie, R. C., Lindsay, B. G., Rutledge, P. S., Woodgate, P. D., J. Chem. Soc. Chem. Comm. (1978) 919.] formed by reaction of the α-iodo derivative with meta-chloroperbenzoic acid in the presence of an excess of the appropriate alcohol gives these derivatives. Final glycosylation by standard methodology and deblocking affords the final glycyrrhetinic acid conjugate.

The compound can be inverted from the β to the α from i.e. the $C_3$-β-OH to the $C_3$-α-OH using the Mitsunobu method (Mitsunobu, O. Synthesis (1981), 1) followed by standard glycosylation procedures.

In the case of Example 1, a further manipulation of a glycerol linking arm is necessary to give a 2'-O-glycosylated derivative. This can be accomplished by using the partial protection method developed by Garegg and Hultberg [Garegg, P. J., Hultberg, H., Carbo. Res. 93 (1981) C10-C11.] involving reductive ring opening of a 2',3'-benzylidene acetal with sodium cyanoborohydride in THF.

Acetates and benzoates serve as protecting groups for the hydroxyl groups in sugars and display neighboring group participation in glycosidation reactions. Thus, by judicious choice of protecting groups prior to the glycosidation, i.e., benzyl ethers, acetates or benzoates, one can preferentially select for either the alpha- or beta-glycosides (H. Paulsen, ANGEW Chem. Int. Ed. Engl., 21:155 (1982); R. R. Schmidt, "Synthesis of Glycosides in Comprehensive Organic Synthesis", Ed. B. M. Trost, 6:33–64)

In some instances, a benzyl ester protecting group can be used for the protection of the E-ring carboxyl group, with subsequent removal will also provide reduction of the 11-carbonyl function to afford 11-deoxoglycyrrhetinic acid conjugates (see Examples 1, 2 and 3). It is known that glycyrrhetinic acid and its derivatives have an aldosterone (DCA)-like activity and promote sodium retention and potassium excretion, which may induce edema, a decrease in serum potassium level, a rise in blood pressure and myopathy. 11-deoxoglycyrrhetinic acid does not substantially show the DCA activity of the parent compound, however [Baren, J. S., et al., J. Med. Chem. 17(2) (1974) 184–191]. Thus, in one operation, the various derivatives are converted to potentially more useful compounds.

The synthesis of other compounds containing alternate linking arms for the glycoside conjugates are accomplished by several methods. The mercaptoethanol linked derivatives(Examples 4 and 8) can be synthesized by initial synthesis of a 2-bromoethanol ether of the 3β-glycyrrhetinic acid skeleton. This type of derivative can then be reacted with an in situ generated, protected 1-thio-sugar by the methodology of Cerny and Pacak [Cerny, M., Pacak, J., Coll. Czeck. Chem. Commun. 24 (1959) 2566–2569]. Ethanolamine linked glycoside conjugates (see Example 3) are synthesized by reductive amination of a 3-keto derivative with ethanolamine followed by glycosylation by standard means. Alternately, a carbohydrate (α-L-fucose) is utilized as a linking group between a pyran ring and the glycyrrhetinic acid nucleus by a selective protection methodology involving use of a 3,4-benzylidene derivative (see Example 2).

Multivalent Forms of the Receptor Binding Ligands

The affinity of the ligands of the invention for a receptor can be enhanced by providing multiple copies of the ligand in close proximity, preferably using a scaffolding provided by a carrier moiety. It has been shown that provision of such multiple valence with optimal spacing between the moieties dramatically improves binding to a receptor. (See, for example, Lee, R. et al., Biochem (1984) 23:4255).

The multivalency and spacing can be controlled by selection of a suitable carrier moiety. Such moieties include molecular supports which contain a multiplicity of functional groups that can be reacted with functional groups associated with the ligands of the invention. A particularly preferred approach involves coupling of the ligands of the invention to amino groups of the carrier through reductive amination. Reductive amination is a particularly convenient way to couple aldehyde moieties to free amino groups by first forming the Schiff base and then treating the conjugate with a reducing agent, such as a hydride reducing agent. Typically, the amino group-bearing carrier is mixed with the carbohydrate moiety at about pH 9 and allowed to form the Schiff base; the solvents are typically evaporated and a reducing agent is added at high pH to complete the reaction.

Particularly convenient carrier moieties to obtain multivalent forms of the invention ligands include (amines (e.g. $N(\sim NH_2)_3$), proteins and peptides, particularly those containing lysyl residues which have $\epsilon$-amino groups available for binding. It is also useful to include in the peptide or protein at least one tyrosine residue, as this offers a convenient site for labeling, for example with radioactive iodine. A particularly convenient carrier to obtain a trivalent couple is the peptide Lys-Tyr-Lys. Complete reaction of the ligands of the invention with the free amino groups on this peptide result in a trivalent moiety. Thus, compounds of the invention of the general formula (I) may be used to make multivalent constructs:

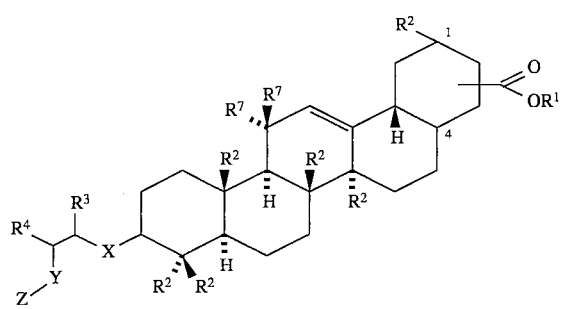

Attachments of the ligand to the amine, or vice versa, by reductive amination would produce multivalent compounds. Preferred attachment points would be at $R^1$, $R^3$, $R^4$, $R^7$, X, Y and Z. Particularly at positions $R^3$, $R^4$ and $R^7$.

Of course, a variety of carriers can be used, including proteins such as BSA or HSA, a multiplicity of peptides including, for example, pentapeptides, decapeptides, pentadecapeptides, and the like. Preferably, the peptides or proteins contain the desired number of amino acid residues having free amino groups in their side chains; however, other functional groups, such as sulfhydryl groups or hydroxyl groups can also be used to obtain stable linkages. For example, the carbohydrate ligands of the invention may be oxidized to contain carboxyl groups at the reducing terminus which can then be derivatized with either free amino groups to form amides or with hydroxyl groups to form esters.

EXAMPLES

The following examples are put forth so as to provide those of ordinary skill in the art with a complete disclosure and description of how to make the compounds and compositions of the invention and are not intended to limit the scope of what the inventors regard as their invention. Efforts have been made to ensure accuracy with respect to numbers that would be used (e.g., amounts, temperature, etc.) but some experimental errors and deviations should be accounted for. Unless indicated otherwise, parts are parts by weight, molecular weight is weight average molecular weight, temperature is in degrees centigrade and pressure is at or near atmospheric.

Example 1

Preparation of a Compound Containing a β-D-Xyloside Unit Attached to the 3β-Position of 11-Deoxoglycyrrhetinic Acid by a 2'-Glycerol Bridge.

The following compound is prepared:

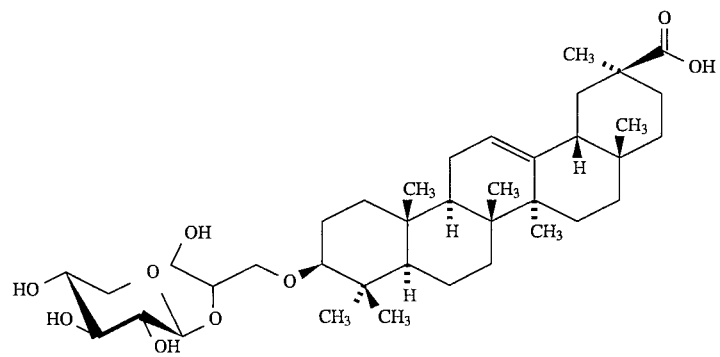

2,3,4-Tri-O-Acetyl α-D-Xylopranosyl Bromide.

To a solution of 45% hydrobromic acid in glacial acetic acid (150 mL), cooled to 0° C. (ice-bath), is added β-D-xylopyranose, tetraacetate (solid, 49.88 g, 156.7 mmole) and this solution is allowed to stir at 0° C. for 2 hours and at ambient temperature for 2.5 hours until the solid has gone completely into solution. The solution is diluted with chloroform (200 mL) and extracted with ice cold water (1×250 mL). The aqueous layer is back-extracted with fresh chloroform (2×60 mL). The combined organic layers are extracted successively with ice-cold saturated aqueous sodium bicarbonate solution (1×250 mL), and ice water (1×250 mL). The chloroform layers are dried over anhydrous sodium sulfate, filtered, and evaporated under reduced pressure. The remaining off-white solid is dried in vacuo. An analytical sample can be purified by crystallization from hot diethylether (200 mL) giving colorless needles.

3β-Hydroxy-11-oxo-18β-olean-12-en-30-oic Acid, Benzyl Ester (1a).

The benzyl ester of glycyrrhetinic acid is prepared by a modification of the method of Baran, et al. [Baran, J. S., Langford, D. D., Liang, C. D., Pitzele, B. S., *J. Med. Chem.* 17(2) (1974) 184–191.]. To a cooled solution (0° C., ice bath) of glycyrrhetinic acid (10.0 g, 21.3 mmole) in anhydrous methanol (70 mL) is added a solution of freshly prepared sodium methoxide (1.074N, 20.0 mL). The reaction mixture is allowed to warm to room temperature, evaporated to dryness and dried in vacuo for two hours. The resulting salt is suspended in anhydrous benzene (200 mL) containing benzyl chloride (2.50 mL, 21.7 mmole). This solution is heated to reflux for 1 hour, cooled, evaporated and dried in vacuo. The residue is purified by column chromatography on a column of silicagel G; elution using a gradient of 0 to 15% methanol in chloroform.

3α-Iodo-11-oxo-18β-olean-12-en-30-oic Acid, Benzyl Ester (1b).

The 3α-iodo derivative of glycyrrhetinic acid, benzyl ester is prepared by a similar method to that used by Greenhouse and Muchowski [Greenhouse, R., Muchowski, J. M., *Can. J. Chem.* 59 (1981) 1025–1027] for the synthesis of 3-desoxy-3α-iododigitoxigenin. To a solution of 12.69 g (0.05 mole) of iodine in anhydrous benzene (35 mL) is added a solution of triphenylphosphine (13.12 g, 0.05 mole) in dry benzene (50 mL). After the solution became pale, an abundant yellow precipitate of triphenylphosphine diiodide is produced. To this solution is added directly glycyrrhetinic acid, benzyl ester (1a) (5.60 g, 0.01 mole) and this suspension is heated to reflux with stirring for 24 hours. After cooling, the reaction mixture is mixed with ice-water (60 mL) and extracted. The benzene layer is further extracted with water (2×100 mL), dried over anhydrous sodium sulfate, evaporated and dried in vacuo to an off white solid. This residue is triturated with n-pentane (200 ml) and the insoluble triphenylphosphine oxide filtered. After rotary evaporation of the pentane solvent, the product is recrystallized from toluene:acetone.

3β-(2',3'-Dihydroxypropoxy)-11-oxo-18β-olean-12-en-30-oic Acid, Benzyl Ester (1c).

60% meta-Chloroperbenzoic acid (450 mg), is added in one portion to a stirred solution of the 3α-iodo compound (1b) (1.00 g, 1.50 mmole) and glycerol acetonide (25 mL) in dry dichloromethane (25 mL). After 1 hour, methanol (100 mL) and 0, 1N sulfuric acid (50 mL) are added and the mixture stirred for an additional 4 hours. This mixture is made neutral by addition of solid sodium bicarbonate, concentrated in vacuo to remove most of the methanol, and partitioned between ethyl acetate and water. The organic phase is washed with water, dried over anhydrous sodium sulfate and evaporated. The residue is dissolved in dichloromethane and applied to a column of silicagel G (150 g). Elution with diethylether (500 mL) removes nonpolar material and subsequent elution with ethyl acetate (500 mL) gives the partially purified product. Final purification is performed using an HPLC system (eluent=8:1 ethylacetate:hexanes; flow rate=12 mL/min. at 1500 psig.)

3β-(2',3'-Benzylidene-dihydroxypropoxy)-11-oxo-18β-olean-12-en-30-oic Acid, Benzyl Ester (1d).

To a solution of the 3β-glycerol glycyrrhetinate benzyl ester (1c) (634 mg, 1.0 mmole) and α,α-dimethoxytoluene (240 μL, 1.6 mmole) in anhydrous acetonitrile (6 mL) is added p-toluenesulfonic acid, mono-hydrate (20 mg, 0,1 mmole) and this solution allowed to stir at room temperature under an atmosphere of dry nitrogen gas for 18 hours. The reaction is quenched with dry triethylamine (15 μL), evaporated to dryness and dried in vacuo to an off white solid, which is applied to a column of silicagel G (100 g) and eluted with toluene:acetone (gradient 0–35% acetone). Fractions containing the pure fully protected derivative are combined and evaporated to dryness.

3β-(3'-O-Benzyl-2'-hydroxypropoxy)-11-oxo-18β-olean-12-en-30-oic Acid, Benzyl Ester (1e).

Reductive ring opening of the 2,3-benzylidene compound (1d) is accomplished by the method of Garegg and Hultberg [Garegg, P. J., Hultberg, H., *Carbo. Res.* 93 (1981) C10–C11.]. A solution of the benzylidene acetal (1d) (600 mg, 0.83 mmole), in tetrahydrofuran containing sodium cyanoborohydride (7.5 mL of a 1.0M solution) and powdered 3A molecular sieves is cooled to 0° C. (ice-bath). One crystal of methyl-orange indicator is added to the reaction to help monitor the pH. A solution of saturated hydrochloric acid in anhydrous diethyl ether is added dropwise slowly until a permanent red color is observed and all evolution of hydrogen gas from the reaction ceases. The reaction mixture is poured into ice-water and the product extracted with dichloromethane (3×25 mL). The combined extracts are washed with saturated sodium bicarbonate solution (2×40 mL) and water (1×50 mL), dried over anhydrous sodium sulfate, filtered, evaporated to dryness and dried in vacuo. The product is purified by chromatography (silicagel G column, 100 g) with elution using a toluene:acetone gradient (0–20%).

3β-(3'-O-Benzyl-2'-O-[2,3,4-tri-O-acetyl-β-D-xylopyranosyl]propoxy)-11-oxo-18β-olean-12-en-30-oic Acid, Benzyl Ester (1f).

Under anhydrous conditions, a solution of the 3'-O-benzyl-2'-hydroxyglyceryl ether of glycyrrhetinic acid, benzyl ester (1e) (500 mg, 0.69 mmole), symcollidine (228 μL, 1.73 mmole), powdered, activated 4A molecular sieves (0.5 g) and anhydrous silver carbonate (477 mg, 1.73 mmole) in anhydrous dichloroethane (25 mL) is allowed to stir in the dark under a atmosphere of dry nitrogen gas for 1 hour. Solid 1-bromo-1-deoxy-2,3,4-tri-O-acetyl-α-D-xylopyranose (0.70 g, 1.73 mmole) is added to the above solution slowly with stirring over a period of 15 minutes. The above mixture is allowed to stir at room temperature, as above for 48 hours, filtered through a Celite™ or diatomaceous earth pad, and the precipitate washed with excess chloroform. The combined filtrates are extracted with water (1×100 mL), ice-cold 1N aqueous HCl (2×100 mL), saturated sodium bicarbonate solution (2×100 mL), 0.1N aqueous sodium thiosulfate solution (1×100 mL) and brine solution (1×100 mL). Each aqueous layer is back-extracted with fresh chloroform (5 mL), and the combined organic layers dried over anhydrous sodium sulfate, filtered, and evaporated under reduced pressure to a syrup. This crude product is applied to a silicagel G chromatography column (250 g) and eluted by gradient elution using 50% to 10% hexanes in chloroform as eluent. Fractions containing the product are combined and evaporated in vacuo to an off-white powder.

3β-(3'-O-Benzyl-2'-O-[β-D-xylopyranosyl]propoxy)-11-oxo-18β-olean-12-en-30-oic Acid, Benzyl Ester (1g).

A solution of the protected 2'-O-glycerolxyloside conjugate of 3β-glycyrrhetinic acid, benzyl ester (1f) (510 mg, 0.52 mole) is suspended in anhydrous methanol (100 mL) and cooled to 0° C. (ice-bath) while under an atmosphere of dry nitrogen gas. To this suspension is added freshly prepared sodium methoxide/methanol solution (1.0 mL, 1.032N solution). The reaction is allowed to stir under anhydrous conditions at 0° C. for 2 hours and at room temperature for 5 hours, neutralized with washed, dry IRC50(H+) resin (to pH 6), filtered, and the resin washed repeatedly with methanol. The combined filtrates are evaporated and dried in vacuo to give the title compound, homogeneous by t.l.c.

3β-(2'-O-[β-D-xylopyranosyl]-3'-hydroxypropoxy)-18β-olean-12-en-30-oic Acid (1h).

A stirred solution of the benzyl ester (1 g) (250 mg, 0.29 mmole) in methanol (30 mL) is catalytically hydrogenated over 10% Pd-carbon (90 mg) at atmospheric pressure overnight. The catalyst is filtered off through a 0.45μ membrane filter, and the filtrate concentrated and dried in vacuo. The resulting solid is crystallized from methanol:diethylether to give a white powder.

Example 1 (Alternate)

3β-(2'-O-[β-L-fucopyranosyl]-3'-[β-L-fucopyranosyl]-18β-olean-12-en-30-oic Acid

Dissolve 18-β-Glycyrrhetinic Acid (2.0 gm, 4.75 mmol) in tetrahydrofuran (4.75 ml) and carefully add hexane washed sodium hydride (0.61 gm, 25.5 mmol). Stir the suspension at ambient temperature for 30 minutes then dilute to 0.5M with 4.25 mL DMF.

Add allylbromide (2.06 gm, 17.0 mmol) dropwise followed by tetrabutylammonium iodide (157 mg, 0.425 mmol) and stir the reaction contents at ambient temperature for 12 hrs.

Warm the reaction to reflux for 4 hrs., cool to ambient temperature, carefully quench with methanol (10 ml), and stir an additional 1 hr.

Dilute the contents with chloroform (100 ml) and wash with water (2.25 ml), 1.0M HCl (2×25 ml), saturated sodium bicarbonate solution (2×25 ml) and brine (2×25 ml), dry over anhydrous sodium sulfate, filter and remove the solvent in vacuo.

Precipitate the crude product from methanol or purify by column chromatography (ratio of 20:1) and elute with toluene and then gradient to 30% ethylacetate in hexanes. Recover 3-β-O-allyl-18-β-glycyrrhetinic acid allyl ester and 18-β-glycyrrhetinic acid allyl ester.

Dissolve the 3-β-O-allyl-18-β-Glycyrrhetinic acid allylester (1.0 gm, 1.81 mmol) in dichloromethane (0.2 m, 9.1 ml) and add 4-methyl-morpholine N-oxide (18.1 mmol, 2.12 gm) followed by osmium tetroxide (0.18 mmol 363 μl of a 0.5M in toluene) and stir the reaction contents at ambient temperature for 24 hours (TLC 30% EtoAc/Hexane).

Quench the reaction with aqueous sodium bicarbonate, extract with chloroform, wash with water (2×25 ml) 1.0M HCl (2×25 ml) sodium bicarbonate (2×25 ml) and brine (2×25 ml), dry over anhydrous sodium sulfate, filter and remove the solvent in vacuo.

Dissolve the crude product in tetrahydrofuran and add 8M NaOH (20 ml) and stir the reaction contents at ambient temperature (12 hrs.), TLC 5% methanol chloroform carefully quenched with 1.0M HCl until reaching pH 3–4, remove the solvent in vacuo dissolve in methanol, filtered salts, remove solvent in vacuo and precipitate product with acetone.

Dissolve 3-β-(2¹-R/S-3¹-Propanediol)-18-β-Glycyrrhetinic acid (500 mg 0.865 mmol) in dichloromethane (4.3 ml, 0.2M) under anhydrous conditions. Add powdered 4A molecular sieves (500 mg) along with acetochloro-α-L-fucose (668 mg, 2.16 mmol). Add silver trifluoromethane sulfonate (556 mg, 2.16 mmol) in one portion and stir the reaction contents at ambient temperature and protect from light for 12 hrs.

Quench the reaction with aqueous sodium thiosulfate (10 ml), stir 30 minutes, then add 10 ml 1.0M HCl and stir until the dichloromethane layer clears. Separate the layers and wash the combined dichloromethane layers with water (2×10 ml), brine (2×10 ml), dry over anhydrous sodium sulfate, filter and remove the solvent in vacuo. Dissolve the crude product in methanol and add 8M NaOH. Stir at ambient temperature 12 hrs., then carefully quench with 1.0M HCl until obtaining pH 3–4.

Remove the solvents in vacuo and precipitate the salts with methanol, filter, remove solvent in vacuo and precipitate the crude produce in acetone. Column chromatography 15% methanol chloroform can confirm the desired product.

Example 2

Preparation of a Compound Containing a 2-O-Tetrahydropyranyl Substituted α-L-Fucopyranoside Ring at the 3β-Position of 11-Deoxyglycyrretinic Acid.

The following compound is prepared:

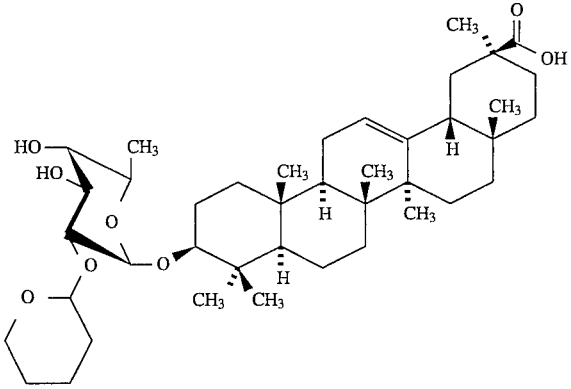

2,3,4-Tri-O-benzyl-α-L-fucopyranosyl Bromide.

The activated fucose derivative is prepared from 2,3,4-tri-O-benzyl-1-O-p-nitrobenzoyl-β-L-fucopyranose by a method similar to that used by Dejter-Juszynski and Flowers [Dejter-Juszynski, M. and Flowers, H. M., Carbo. Res. 18 (1971) 219].

3β-O-(2,3,4-tri-O-benzyl-α-L-fucopyranosyl)-11-oxo-18β-olean-12-en-30-oic Acid, Benzyl Ester (2a).

Under anhydrous conditions, a solution of the glycyrrhetinic acid, benzyl ester (1a) (1.00 g, 1.79 mmole), tetraethylammonium bromide (380 mg, 1.81 mmole), diisopropylethylamine (Hünigs base, 315 μL, 1.81 mmole) and powdered, activated 3A molecular sieves (0.5 g) in anhydrous DMF (4 mL) and dichloromethane (20 mL) is stirred at room temperature for 30 min. To this solution is added freshly prepared 2,3,4-tri-O-benzyl-α-L-fucopyranosyl bromide (2.09 g, 3.58 mmole). This solution is allowed to stir as above at room temperature for 3 days, after which time t.l.c. analysis shows that all of 2a has been consumed. The solution is diluted with dichloromethane (100 mL), and extracted with water (2×100 mL), saturated aqueous sodium bicarbonate solution (1×100 mL), saturated brine solution (1×100 mL) and water (1×100 mL). The combined organic layers are dried over anhydrous sodium sulfate, filtered, evaporated and dried in vacuo to a pale yellow syrup, which is used directly for the preparation of 2b.

3β-O-(α-L-fucopyranosyl)-18β-olean-12-en-30-oic Acid (2b).

A stirred solution of the benzyl ester (2a) (1.64 g, 1.68 mmole) in ethanol (75 mL) is catalytically hydrogenated over 10% Pd-carbon (125 mg) at atmospheric pressure for 2 days. The catalyst is filtered through a 0.45μ membrane filter, and the filtrate concentrated and dried in vacuo. The resulting solid is crystallized from ethanol:diethylether to give a white powder.

Benzyl, 3β-O-(α-L-fucopyranosyl)-18β-olean-12-en-30-oate (2c).

The fucoside (2b) (982 mg, 1.63 mmole) is dissolved in anhydrous acetonitrile (50 mL) containing dicyclohexylcarbodiimide (340 mg, 1.65 mmole) and recrystallized N,N-dimethylaminopyridine (40 mg) under anhydrous conditions. To this solution is added benzyl alcohol (1.75 mL, 16.9 mmole), and this solution allowed to stir at room temperature as above overnight, filtered, evaporated to dryness and dried in vacuo. The resulting solid is purified by column chromatography on a short bed of silicagel G (100 g) with elution using ethylacetate:methanol as solvent. Fractions containing the purified product are combined and evaporated to an off-white powder.

Benzyl, 3β-O-(3,4-O-benzylidene-α-L-fucopyranosyl)-18β-olean-12-en-30-oate (2d).

To a stirred solution of the benzyl ester (2c) (850 mg, 1.23 mmole) in anhydrous dichloromethane (50 mL) is added α,α-dimethoxytoluene (560 mg, 0.55 mL, 3.69 mmole) and p-toluenesulfonic acid, monohydrate (50 mg). This solution is allowed to stir at room temperature overnight, after which time t.l.c. analysis indicates that all of 2c is converted to a higher t.l.c. mobility product. The reaction is quenched by addition of ice-water (20 mL), diluted with chloroform (100 mL) and extracted with water (1×200 mL), saturated, aqueous sodium bicarbonate solution (2×100 mL), and water (1×100 mL). The organic phases are dried over anhydrous sodium sulfate, filtered and evaporated to dryness. The resulting solid is triturated with anhydrous pentanes to give a white solid.

Benzyl, 3β-O-(3,4-O-benzylidene-2-O-tetrahydropyranyl-α-L-fucopyranosyl)-18β-olean-12-en-30-oate (2e).

Under anhydrous conditions, a mixture of the benzylidene derivative (2d) (780 mg, 1.0 mmole) and 3,4-dihydropyran (183 μL, 2.0 mmole) in dry dichloromethane (25 mL) is treated with washed, dry Amberlyst H-15 ion-exchange resin (1.5 g) at room temperature for 2.5 hours. The resin is filtered, and washed with excess dichloromethane (5×30 mL), allowing the resin to equilibrate with the solvent during each washing. The combined filtrates are evaporated, co-evaporated with anhydrous toluene (4×30 mL), and dried in vacuo overnight to yield a clear glass (859 mg, 99%) which is used without further purification for the synthesis of 2f.

3β-O-(2-O-Tetrahydropyranyl-α-L-fucopyranosyl)-18β-olean-12-en-30-oic Acid (2f).

A stirred solution of the fully protected benzyl ester (2a) (850 mg, 0.98 mmole) in a mixture of dry benzene (30 mL) and absolute ethanol (30 mL) is catalytically hydrogenated over 10% Pd-carbon (125 mg) at atmospheric pressure for 37 hours. The catalyst is removed by filtration through a 0.45μ membrane filter, and the filtrate is concentrated and dried in vacuo. The resulting solid is applied to a gel-filtration column of Sephadex LH-20 (200 g) using water and 5% ethanol/water as eluents. Fractions containing the purified product are combined and evaporated as much as possible at 30° C. under reduced pressure, and the residual water solution is lyophilized to a white foam.

Example 2 (Alternate)

3β-O-(α-L-fucopyranosyl)-18β-olean-12-en-30-oic Acid

Dissolve 18-β-Glycyrrhetinic acid (1.0 gm, 2.12 mmol) in 50% tetrahydrofuran/1,2-dichloromethane (11 ml, 0.2M) under anhydrous conditions. Add powdered 4A molecular sieves (1 gm) along with acetochloro-α-L-fucose (772 mg, 2.34 mmol). Add silver trifluoromethane sulfurate (600 mg, 2.34 mmol) in one portion and stir the reaction contents at ambient temperature and protect from light for 12 hrs.

Quench the reaction with aqueous sodium thiosulfate (20 ml), stir 30 minutes then 1.0M HCl (20 ml) and stir until the dichloromethane layer clears. Separate the layers and wash the combined dichloromethane layers with water (2×25 ml), 1.0M HCl (2×25 ml) saturated sodium bicarbonate (2×25 ml) brine (2×25 ml), dry over anhydrous sodium sulfate, filter and remove the solvent in vacuo. Dissolve the crude product in methanol and add 8M NaOH. Stir at ambient temperature for 12 hrs., then carefully quench with 1.0M HCl until pH 3–4.

Remove the solvents in vacuo and precipitate the salts with methanol, filter, and remove the solvent in vacuo. The crude product can be purified by chromatography (silica gel 20:1) and eluted with 15% methanol chloroform.

Example 3

Preparation of a Compound Containing a β-D-Glucopyransiduronic Acid Unit Attached to 3β-Position of 11-Deoxyglycyrrhetinic Acid by an Ethanolamine Bridge.

The following compound is prepared:

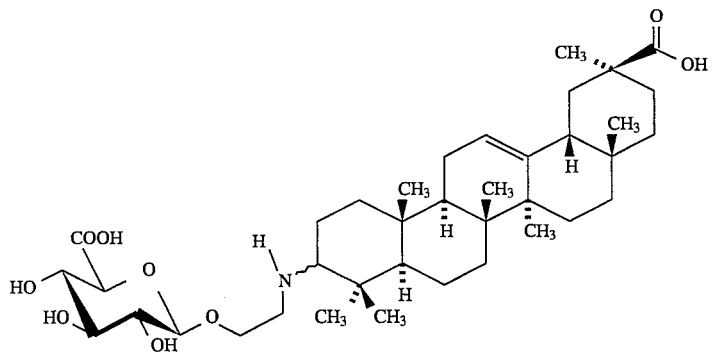

Methyl, 3β-Hydroxy-11-oxo-18β-olean-12-en-30-oate (3a).

To a solution of glycyrrhetinic acid (25.0 g, 53.23 mmole) in anhydrous methanol (300 mL) is added washed, vacuum dried Dowex™50WX12 (H+) resin (10 g) and this mixture is allowed to stir at ambient temperature for 6 hours until t.l.c. indicates that all of the starting acid has been converted to a higher t.l.c. mobile product. The supernatent solution is decanted, and the resin is treated with fresh anhydrous methanol (100 mL). This solution is allowed to stir as above for 1.5 hours, filtered through a sintered glass Buchner funnel, and the resin was repeatedly washed with methanol (5×20 mL), allowing the resin to equilibrate with the solvent during each wash. The combined methanol filtrates are evaporated to dryness and dried in vacuo to a colorless solid which is homogeneous by t.l.c. This material is used without further purification for the production of compound 3b.

Methyl, 3β-Hydroxy-18β-olean-12-en-30-oate (3b).

A stirred solution of the methyl ester (3a) (5.0 g, 10.34 mmole) in methanol (30 mL) is catalytically hydrogenated over 10% Pd-carbon (250 mg) at atmospheric pressure overnight. The catalyst is filtered through a 0.45μ membrane filter, and the filtrate is concentrated and dried in vacuo, to give a white powder.

Methyl, 3-Oxo-18β-olean-12-en-30-oate (3c).

The 11-deoxyglycyrrhetinic acid, methyl ester (3b) is oxidized with chromic acid according to the procedure of Baran, et al. [Baran, J. S., Langford, D. D., Liang, C. D., Pitzele, B. S., *J. Med. Chem.* 17(2) (1974) 184–191]. To an ice-cold solution of 3b (4.70 g, 10.0 mmole) in dry acetone (500 mL) is added slowly with stirring an ice cold $CrO_3$-$H_2SO_4$ solution (8N solution), until the acetone solution becomes a permanent dark brown color. Stirring is continued for 1 hour as above. The solution is decanted from the resulting green gum, and diluted with water (to 1.5 L). This mixture was extracted with ethylacetate:diethylether (1:1, 5×200 mL). The combined organic extracts are washed with water (2×400 mL), saturated brine solution (1×250 mL) and dried over anhydrous sodium sulfate. The product is decolorized with charcoal, filtered, and evaporated to a solid which is applied to a column of silicagel G (500 g) and eluted with a solvent gradient consisting of 0–8% ethanol in chloroform. Fractions containing the second major component to elute from the column are combined and evaporated to dryness.

Methyl, 3-(Amino-2'-hydroxyethyl)-18β-olean-12-en-30-oate (3d).

The keto-derivative (3c) (1.20 g, 2.57 mmole) is dissolved in a solution of anhydrous tetrahydrofuran (20 mL) containing ethanolamine (155 μL, 2.57 mmole) and allowed to stir at room temperature for 3 hours. To this mixture is added a solution of sodiumcyanoborohydride in anhydrous tetrahydrofuran (2.6 mL of a 1.0M solution) and this mixture allowed to continue stirring at room temperature until the evolution of hydrogen gas has ceased and for an additional 2 hours. The reaction is quenched with water (4 mL) and evaporated to dryness. The crude mixture is applied to a column of silicagel G (150 g) and the product is eluted by gradient elution using 0–15% acetonitrile in chloroform as eluent. Fractions containing the product are evaporated and dried in vacuo to give a clear foam.

Methyl, 3-(Amino-2'-O-[methyl, 2,3,4-tri-O-acetyl-β-D-glucopyranosiduronyl])-18β-olean-12-en-30-oate (3e).

Under anhydrous conditions, a solution of the 3-aminohydroxyethylglycyrrhetinic acid, methyl ester (3d) (1.00 g, 1.95 mmole), sym-collidine (330 μL, 2.5 mmole), powdered, activated 4A molecular sieves (0.5 g) and anhydrous silver carbonate (690 mg, 2.5 mmole) in anhydrous dichloroethane (25 mL) are allowed to stir in the dark under a atmosphere of dry nitrogen gas for 1 hour. Solid methyl 1-bromo-1-deoxy-2,3,4-tri-O-acetyl-α-D-glucopyranosiduronate (1.00 g, 2.5 mmole) is added to the above solution slowly with stirring over a period of 15 minutes. The above mixture is allowed to stir at room temperature, as above for 82 hours, filtered through a Celite™ or diatomaceous earth pad, and the precipitate washed with excess chloroform. The combined filtrates are extracted with water (1×100 mL), ice-cold 1N aqueous HCl (2×100 mL), saturated sodium bicarbonate solution (2×100 mL), 0.1N aqueous sodium thiosulfate solution (1×100 mL) and brine solution (1×100 mL). Each aqueous layer is back-extracted with fresh chloroform (5 mL), and the combined organic layers are dried over anhydrous sodium sulfate, filtered, and evaporated under reduced pressure to a syrup. This crude product is applied to a silicagel G chromatography column (250 g) and eluted by gradient elution using 0–20% ethylacetate in chloroform as eluent. Fractions containing the product are combined and evaporated in vacuo to an off-white powder.

Methyl, 3-(Amino-2'-O-[methyl, β-D-glucopyranosiduronyl])-18β-olean-12-en-30-oate (3f).

A solution of the fully protected 2-aminoethoxy glucuronide conjugate of 3-glycyrrhetinic acid, methyl ester (3e) (1.30 g, 1.57 mole) is suspended in anhydrous methanol (200 mL) and cooled to 0° C. (ice-bath) while under an atmosphere of dry nitrogen gas. To this suspension is added freshly prepared sodium methoxide/methanol solution (1.5 mL, 1.243N solution). The reaction is allowed to stir under anhydrous conditions at 0° C. for 2 hours and at room temperature for 2 hours. The reaction is then neutralized with washed, dry IRC50(H+) resin (to pH 6), filtered, with the resin being washed repeatedly with methanol. The combined filtrates are evaporated and dried in vacuo to give the title compound as a white solid, homogeneous by t.l.c.

3-(Amino-2'-O-[β-D-glucopyranosiduronyl])-18β-olean-12-en-30-oic Acid (3q).

A solution of the partially protected 2-aminoethoxy glucuronide conjugate of 3-glycyrrhetinic acid, methyl ester (3f) (1.00 g, 1.42 mmole) in tetrahydrofuran (50 mL) and water (10 mL) is treated with 1.0N aqueous lithium hydroxide solution (7 mL) in portions at room temperature. After 2 hours, the reaction is neutralized with washed IRC50(H+) resin, filtered and the resin washed repeatedly With methanol and water. The combined filtrates are evaporated and coevaporated with ethyl alcohol (2×20 mL) and the final aqueous solution is lyophilized to an off-white foam. This final sample is purified by Sephadex LH20 column chromatography with elution using water and 5% ethanol/water as eluents.

Example 4

Preparation of a Compound Containing a 1-Deoxy-1-Thio β-L-Rhamnopyranosyl Unit Attached to the 3β-Position of Glycyrrhetinic Acid by a Two Carbon Bridge.

The following compound is prepared:

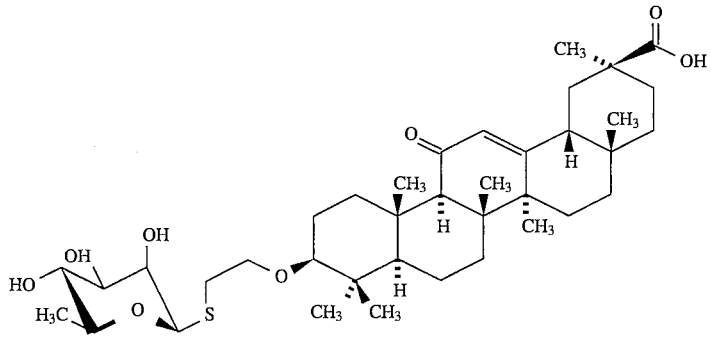

3α-Iodo-11-oxo-18β-olean-12-en-30-oic Acid, Methyl Ester (4a).

The 3α-iodo derivative of glycyrrhetinic acid, methyl ester is prepared by a method similar to that used above for the preparation of the analogous benzyl derivative (see Example 1) [Greenhouse, R., Muchowski, J. M., *Can. J. Chem.* 59 (1981) 1025–1027]. To a solution of 12.69 g (0.05 mole) of iodine in anhydrous benzene (35 mL) is added a solution of triphenylphosphine (13.12 g, 0.05 mole) in dry benzene (50 mL). After the solution becomes pale, an abundant yellow precipitate of triphenylphosphine diiodide is produced. To this solution is added directly glycyrrhetinic acid, methyl ester (1a) (4.84 g, 0.01 mole) and this suspension is heated to reflux with stirring for 18 hours. After cooling, the reaction mixture is mixed with ice-water (60 mL) and extracted. The benzene layer is further extracted with water (2×100 mL), dried over anhydrous sodium sulfate, evaporated and dried in vacuo to an off white solid. This residue is triturated with n-pentane (200 ml) and the insoluble triphenylphosphine oxide filtered. After rotary evaporation of the pentane solvent, the product is recrystallized from toluene:acetone.

3β-(2'-Bromoethoxy)-11-oxo-18β-olean-12-en-30-oic Acid, Methyl Ester (4b).

60% meta-Chloroperbenzoic acid (450 mg), is added in one portion to a stirred solution of the 3α-iodo compound (4a) (4.80 g, 8.09 mmole) and 2-bromoethanol (15 mL, 26.45 g, 25 equivalents) in dry dichloromethane (100 mL). After 4 hours this mixture is made neutral by addition of solid sodium bicarbonate, concentrated in vacuo, and partitioned between ethyl acetate and water. The organic phase is washed with water, dried over anhydrous sodium sulfate and evaporated. The residue is dissolved in dichloromethane and applied to a column of silicagel G (500 g). Elution with diethylether (500 mL) removes nonpolar material and subsequent elution with ethyl acetate (500 mL) gives the partially purified product. Final purification is performed using an HPLC system (eluent=8:1 ethylacetate:hexanes; flow rate=12 mL/min. at 1500 psig.)

1-Deoxy-1-thiouridium-2,3,4-tri-O-acetyl-β-L-rhamnopyranoside, Hydrobromide Salt.

A solution of L-rhamnose monohydrate (6-deoxy-L-mannose, 25.0 g, 0.137 mole) is dissolved in a mixture of acetic anhydride and dry pyridine (1:1, 125 mL) and allowed to stir at room temperature in the absence of moisture overnight. The resulting mixture is diluted with dry toluene (100 mL) and evaporated in vacuo and coevaporated with dry toluene (4×40 mL) to a clear oil which is dried in vacuo, redissolved in fresh chloroform (100 mL) and extracted with water (1×100 mL), 1N aqueous HCl (1×100 mL), saturated aqueous sodium bicarbonate solution (1×100 mL) and water (1×100 mL). The final organic layer is dried over anhydrous sodium sulfate, filtered, evaporated and dried in vacuo overnight.

The residual foam is resuspended in 45% hydrobromic acid/glacial acetic acid (100 mL) at 0° C. and allowed to stir at this temperature for 2 hours and at room temperature overnight. The resulting mixture is diluted with chloroform (200 mL) and extracted with ice-cold water (1×200 mL), ice-cold saturated aqueous sodium bicarbonate solution (4×150 mL) and water (1×200 mL). The organic phase is dried over anhydrous sodium sulfate, filtered, and evaporated to a clear pale yellow oil, which is dried in vacuo.

The crude acetobromorhamnoside is dissolved in dry acetone (40 mL) and heated to near reflux, and addition of the solid thiourea (10.66 g, 0.14 mole) to this hot solution is made in portions with stirring. After an additional heating for 15 minutes, the product begins to crystallize out of the reaction mixture. The reaction is cooled to room temperature and further cooled in an ice-bath to complete crystallization. The product is filtered and dried in air and in vacuo to give an off-white powder. Second and third fractions from concentration of the filtrate give an additional product.

3β-(2'-[2,3,4-tri-O-acetyl-1,6-dideoxy-1-thio-β-L-mannopyranosyl]ethoxy)-11-oxo-18β-olean-12-en-30-oic Acid, Methyl Ester (4c).

The thioglycoside (4c) is prepared by a procedure similar to that used by Cerny and Pacak [Cerny, M., Pacak, J., *Coll. Czeck. Chem. Commun.* 24 (1959) 2566–2569]. To a suspension of the pseudourea (1-deoxy-1-thiouridium-2,3,4-tri-O-acetyl-β-L-rhamnopyranoside, hydrobromide salt, 3.00 g, 7.0 mmole) and the bromoethyl ether (4b) (4.11 g, 6.96 mmole) in dry acetone (50 mL) is added an aqueous solution of potassium carbonate (1.93 g, 14 mmole) and sodium hydrosulfite (1.34 g, 7.7 mmole). This reaction mixture is allowed to stir at room temperature for 30 minutes, and additional saturated potassium carbonate solution is added to adjust the pH to approximately 9.0. The reaction is allowed to stir for an additional 3 hours, quenched by addition of crushed ice (100 mL) and the product extracted with chloroform (5×50 mL). The combined chloroform layers are dried over anhydrous sodium sulfate, filtered, evaporated and dried in vacuo to a white solid. This crude product is purified by column chromatography to give a final product as a clear foam.

3β-(2'-[1,6-dideoxy-1-thio-β-L-mannopyranosyl]ethoxy)-11-oxo-18β-olean-12-en-30-oic Acid, Methyl Ester (4d).

A solution of the fully protected 2-thioethoxy rhamnoside conjugate of 3β-glycyrrhetinic acid, methyl ester (4c) (3.50 g, 4.29 mmole) is suspended in anhydrous methanol (350 mL) and cooled to 0° C. (ice-bath) while under an atmosphere of dry nitrogen gas. To this suspension is added freshly prepared sodium methoxide/methanol solution (2.0 mL, 0.911N solution). This reaction mixture is allowed to stir under anhydrous conditions at 0° C. for 2 hours and at room temperature for 4.5 hours. The reaction is neutralized with washed, dry IRC50(H+) resin (to pH 6), filtered, and the resin washed repeatedly with methanol. The combined filtrates are evaporated and dried in vacuo to give the title compound.

3β-(2'-[1,6-dideoxy-1-thio-β-L-mannopyranosyl]ethoxy)-11-oxo-18β-olean-12-en-30-oic Acid (4e).

A solution of the 2-thioethoxy rhamnoside conjugate of 3β-glycyrrhetinic acid, methyl ester (4d) (2.50 g, 3.62 mmole) in tetrahydrofuran (100 mL) and water (25 mL) is treated with 1.0N aqueous lithium hydroxide solution (10 mL) in portions over a period of 2 hours at room temperature. After stirring for an additional 2 hours, the reaction is neutralized with IRC50(H+) resin, filtered and evaporated as much as possible (T<35° C.). The final solution is coevaporated with ethyl alcohol (2×20 mL) to further remove traces of water, and the final aqueous solution is lyophilized to a pale cream colored foam. The final product can be purified by Sephadex LH20 column chromatography, elution using water and 5% ethanol/water as eluents.

Example 5

Preparation of a Compound Containing a β-D-Glucopyranosiduronic Acid Unit Attached to the 3β-Position of Glycyrrhetinic Acid by an Ethylene Glycol Bridge.

The following compound is prepared:

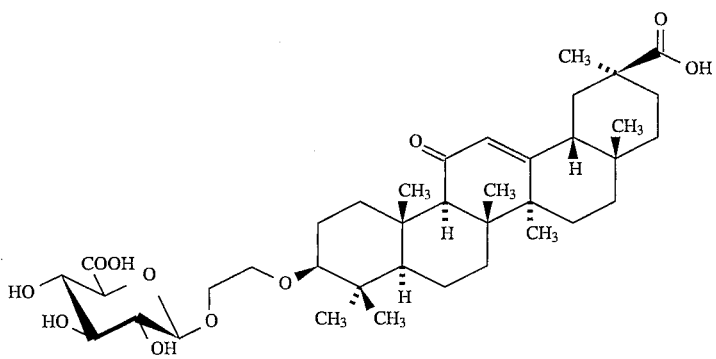

3β-(2-Hydroxyethoxy)-11-oxo-18β-olean-12-en-30-oic Acid, Benzyl Ester (5a).

60% meta-Chloroperbenzoic acid (900 mg), is added in one portion to a stirred solution of the 3α-iodo compound (1b) (2.00 g, 3.0 mmole) and ethylene glycol (10 mL, 179 mmole) in dry dichloromethane (25 mL). After 1.5 hours, the reaction mixture is poured into ice-water (30 mL) and the product is extracted with diethylether (3×25 mL). The combined organic phase is washed successively with water and 5% sodium bicarbonate solution, dried over anhydrous sodium sulfate and evaporated in vacuo. The residue is dissolved in dichloromethane and applied to a column of silicagel G (150 g). Elution with diethylether (500 mL) removes nonpolar material and subsequent elution with hexanes:acetone 7:3 (500 mL) gives the partially purified product. Final purification can be performed by crystallization from ethyl acetate.

3β-(2-O-[Methyl,2,3,4-tri-O-acetyl β-D-glucopyranosiduronyl]ethoxy-11-oxo-18β-olean-12-en-30-oic Acid, Benzyl Ester (5b).

Under anhydrous conditions, a solution of hydroxyethylglycyrrhetinic acid, benzyl ester (5a) (604 mg, 1.0 mmole), sym-collidine (330 μL, 2.5 mmole), powdered, activated 4A molecular sieves (0.5 g) and anhydrous silver carbonate (690 mg, 2.5 mmole) in anhydrous dichloroethane (25 mL) is allowed to stir in the dark under a atmosphere of dry nitrogen gas for 1 hour. Solid methyl 1-bromo-1-deoxy-2,3,4-tri-O-acetyl-α-D-glucopyranosiduronate (1.00 g, 2.5 mmole) is added to the above solution slowly with stirring over a period of 15 minutes. The above mixture is allowed to stir at room temperature, as above for 52 hours, filtered through a celite™ or diatomaceous earth pad, and the precipitate washed with excess chloroform. The combined filtrates are extracted with water (1×100 mL), ice-cold 1N aqueous HCl (2×100 mL), saturated sodium bicarbonate solution (2×100 mL), 0.1N aqueous sodium thiosulfate solution (1×100 mL) and brine solution (1×100 mL). Each aqueous layer is back-extracted with fresh chloroform (5 mL), and the combined organic layers are dried over anhydrous sodium sulfate, filtered, and evaporated under reduced pressure to a syrup. This crude product is applied to a silicagel G chromatography column (250 g) and eluted by gradient elution using 50% to 10% hexanes in chloroform as eluent. Fractions containing the product are combined and evaporated in vacuo to an off-white powder.

3β-(2-O-[Methyl, β-D-glucopyranosiduronate]ethoxy-11-oxo-18β-olean-12-en-30-oic Acid, Benzyl Ester (5c).

A solution of the fully protected 2-ethoxy glucuronide conjugate of 3β-glycyrrhetinic acid, benzyl ester (5b) (300 mg, 0.33 mole) is suspended in anhydrous methanol (50 mL) and cooled to 0° C. (ice-bath) while under an atmosphere of dry nitrogen gas. To this suspension is added a freshly prepared sodium methoxide/methanol solution (600 μL, 0.978N solution). This reaction mixture is allowed to stir under anhydrous conditions at 0° C. for 2 hours and at room temperature for 4 hours. The reaction is neutralized with washed, dry IRC50(H+) resin (to pH 6), filtered, and the resin washed repeatedly with methanol. The combined filtrates are evaporated and dried in vacuo to give the title compound homogeneous by t.l.c.

3β-(2-O-[β-D-Glucopyranosiduronic acid]-ethoxy-11-oxo-18β-olean-12-en-30-oic Acid, Benzyl Ester (5d).

A solution of the partially protected 2-ethoxy glucuronide conjugate of 3β-glycyrrhetinic acid, benzyl ester (5c) (250 mg, 0.31 mmole) in tetrahydrofuran (24 mL) and water (5 mL) is treated with 1.0N aqueous lithium hydroxide solution (3 mL) at room temperature. After 2 hours, the reaction is neutralized with IRC50(H+) resin, filtered and evaporated. The final solution is coevaporated with ethyl alcohol (2×20 mL) to remove traces of water, and dried in vacuo. The final compound is purified by Sephadex LH20 column chromatography; elution using water and 5% ethanol/water as eluents.

3β-(2-O-[β-D-Glucopyranosiduronic acid]-ethoxy-11-oxo-18β-olean-12-en-30-oic Acid (5e).

A stirred solution of the benzyl ester (5d) (150 mg, 0.19 mmole) in methanol (20 mL) is catalytically hydrogenated over 10% Pd-carbon (100 mg) at atmospheric pressure overnight. The catalyst is filtered through a 0.45μ membrane filter, and the filtrate is concentrated and dried in vacuo. The resulting solid is recrystallized from methanol:diethylether to give a white powder.

Example 6

Preparation of a Compound Containing a β-D-Xylopyranosyl Unit Attached to the 3β-Position of Glycyrrhetinic Acid By a cis-Cyclohexanediol Bridge.

The following compound is prepared:

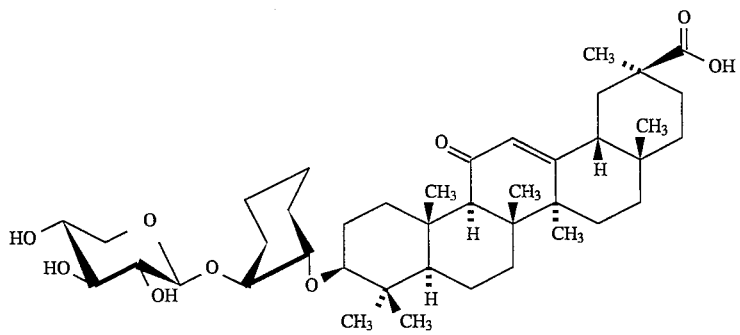

3β-(2-cis-Hydroxycyclohexyloxy)-11-oxo-18β-olean-12-en-30-oic Acid, Benzyl Ester (6a).

60% meta-Chloroperbenzoic acid (900 mg), is added in one portion to a stirred solution of the 3α-iodo compound (1b) (2.00 g, 3.0 mmole) and cis-1,2-cyclohexanediol (17.42 g, 150 mmole) in dry dichloromethane (25 mL). After 1.5 hours, this reaction mixture is poured into ice-water (30 mL) and the product is extracted with diethylether (3×25 mL). The combined organic phase is washed successively with water and 5% sodium bicarbonate solution, dried over anhydrous sodium sulfate and evaporated in vacuo. The residue is dissolved in dichloromethane and applied to a column of silicagel G (150 g). Elution with diethylether (500 mL) removes nonpolar material and subsequent elution with hexanes:acetone 7:3 (500 mL) gives the partially purified product. Final purification is performed by crystallization from ethyl acetate.

3β-(2-O-cis[2,3,4-tri-O-acetyl β-D-xylopyranosyl]cyclohexyloxy-11-oxo-18β-olean-12-en-30-oic Acid, Benzyl Ester (6b)

Under anhydrous conditions, a solution of hydroxycyclohexyloxyglycyrrhetinic acid, benzyl ester (6a) (658 mg, 1.0 mmole), sym-collidine (330 μL, 2.5 mmole), powdered, activated 4A molecular sieves (0.5 g) and anhydrous silver carbonate (690 mg, 2.5 mmole) in anhydrous dichloroethane (25 mL) is allowed to stir in the dark under an atmosphere of dry nitrogen gas for 1 hour. Solid 1-bromo-1-deoxy-2,3,4-tri-O-acetyl-α-D-xylopyranose (1.01 g, 2.5 mmole) is added to the above solution slowly with stirring over a period of about 15 minutes. The above mixture is allowed to stir at room temperature, as above for 4 days, filtered through a Celite™ or diatomaceous earth pad, and the precipitate washed with excess chloroform. The combined filtrates are extracted with water (1×100 mL), ice-cold 1N aqueous HCl (2×100 mL), saturated sodium bicarbonate solution (2×100 mL), 0.1N aqueous sodium thiosulfate solution (1×100 mL) and brine solution (1×100 mL). Each aqueous layer is back-extracted with fresh chloroform (5 mL), and the combined organic layers are dried over anhydrous sodium sulfate, filtered, and evaporated under reduced pressure to a syrup. This crude product is applied to a silicagel G chromatography column (250 g) and eluted by gradient elution using 50% to 10% hexanes in chloroform as eluent. Fractions containing the product are combined and evaporated in vacuo to an off-white powder.

3β-(2-O-cis-[β-D-xylopyranosyl]cyclohexyloxy-11-oxo-18β-olean-12-en-30-oic Acid, Benzyl Ester (6c).

A solution of the protected 2-cyclohexyloxyxyloside conjugate of 3β-glycyrrhetinic acid, benzyl ester (6b) (750 mg, 0.82 mole) is suspended in anhydrous methanol (100 mL) and cooled to 0° C. (ice-bath) while under an atmosphere of dry nitrogen gas. To this suspension is added a freshly prepared sodium methoxide/methanol solution (1.0 mL, 1.124N solution). This reaction mixture is allowed to stir under anhydrous conditions at 0° C. for 2 hours and at room temperature for 5 hours. The reaction is then neutralized with washed, dry IRC50(H+) resin (to pH 6), filtered, and the resin washed repeatedly with methanol. The combined filtrates are evaporated and dried in vacuo to give the title compound.

3β-(2-O-cis-[β-D-xylopyranosyl]cyclohexyloxy-11-oxo-18β-olean-12-en-30-oic Acid (6d).

A stirred solution of the benzyl ester (6c) (500 mg, 0.63 mmole) in ethanol (80 mL) is catalytically hydrogenated over 10% Pd-carbon (100 mg) at atmospheric pressure overnight. The catalyst is filtered through a 0.45μ membrane filter, and the filtrate is concentrated and dried in vacuo. The solid is crystallized from methanol:diethylether to give a white powder.

Example 7

Preparation of a Compound Containing a β-L-Fucopyranosyl Unit Attached to the 3β-Position of Glycyrrhetinic Acid By a 3',4'-Dihydroxybenzoic Acid Bridge.

The following compound is prepared:

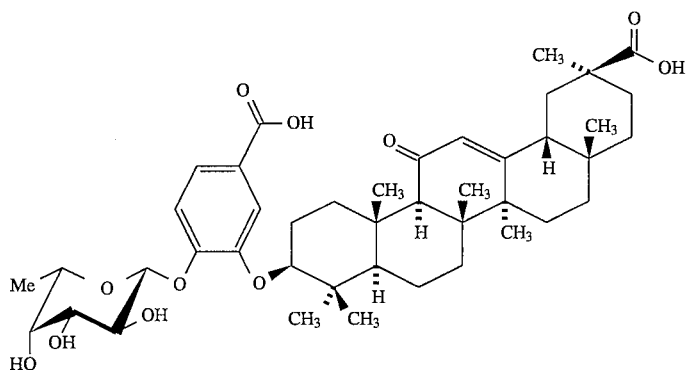

3β-(4'-O-[3'-Hydroxy]methylbenzoate)-11-oxo-18β-olean-12-en-30-oic Acid, Methyl Ester (7a).

60% meta-Chloroperbenzoic acid (450 mg), is added in one portion to a stirred solution of the 3α-iodo compound (4a) (5.00 g, 8.42 mmole) and methyl, 3,4-dihydroxybenzoate (71 grams, 50 equivalents) in dry dichloromethane (500 mL). After 4 hours this mixture is made neutral by addition of solid sodium bicarbonate, concentrated in vacuo, and partitioned between ethyl acetate and water. The organic phase is washed with water, dried over anhydrous sodium sulfate and evaporated. The resulting residue is dissolved in dichloromethane and applied to a flash column of silicagel G (1 Kg) in a sintered glass Buchner funnel. Elution with diethylether (1500 mL) removes nonpolar material and subsequent elution with ethyl acetate (2500 mL) gives the partially purified product. Final purification can be performed using an MPLC system (eluent=8:1 ethylacetate:hexanes; flow rate=12 mL/min. at 400 psig.)

3β-(4'-O-[3'-O-(2,3,4-tri-O-acetyl-β-L-fucopyranosyl]methylbenzoate)-11-oxo-18β-olean-12-en-30-oic Acid, Methyl Ester (7b).

Under anhydrous conditions, a solution of 3'-hydroxymethylbenzoate-glycyrrhetinic acid, methyl ester (7a) (4.00 g, 6.32 mmole), sym-collidine (2.08 mL, 15.78 mmole), powdered, activated 4A molecular sieves (1.0 g) and anhydrous silver carbonate (4.36 g, 15.79 mmole) in anhydrous dichloroethane (100 mL) is allowed to stir in the dark under an atmosphere of dry nitrogen gas for 1 hour. Solid 1-bromo-1-deoxy-2,3,4-tri-O-acetyl-α-L-fucopyranose (4.87 g, 15.79 mmole) is added to the above solution slowly with stirring over a period of 25 minutes. The above mixture is allowed to stir at room temperature, as above for 6 days, after which time analysis by t.l.c. indicates consumption of all 7a. The reaction mixture is then filtered through a Celite™ or diatomaceous earth pad, and the precipitate washed with excess chloroform. The combined filtrates are extracted with water (1×200 mL), ice-cold 1N aqueous HCl (2×200 mL), saturated sodium bicarbonate solution (2×200 mL), 0.1N aqueous sodium thiosulfate solution (1×200 mL) and saturated brine solution (1×200 mL). Each aqueous layer is back-extracted with fresh chloroform (15 mL), and the combined organic layers are dried over anhydrous sodium sulfate, filtered, and evaporated under reduced pressure to a pale yellow syrup. This crude product is applied to a silicagel G chromatography column (2Kg) and eluted by gradient elution using 50% to 10% hexanes in chloroform as eluent. Fractions containing the product are combined and evaporated in vacuo to an off-white powder.

3β-(4'-O-[3'-O-(β-L-fucopyranosyl)]methylbenzoate)-11-oxo-18β-olean-12-en-30-oic Acid, Methyl Ester (7c).

A solution of the protected 3'-methylbenzoyloxyfucoside conjugate of 3β-glycyrrhetinic acid, methyl ester (7b) (3.90 g, 4.30 mmole) is suspended in anhydrous methanol (500 mL) and cooled to 0° C. (ice-bath) while under an atmosphere of dry nitrogen gas. To this suspension is added freshly prepared sodium methoxide/methanol solution (3.0 mL, 0.961N solution). The reaction is allowed to stir under anhydrous conditions at 0° C. for 2 hours and at room temperature for 6 hours. The reaction is neutralized with washed, dry IRC50(H+) resin (to pH 6), filtered, and the resin washed repeatedly with methanol. The combined filtrates are evaporated and dried in vacuo to give the title compound, homogeneous by t.l.c.

3β-(4'-O-[3'-O-(β-L-fucopyranosyl)]benzoate)-11-oxo-18β-olean-12-en-30-oic Acid (7d).

A solution of the partially protected 4'-O-fucosyl-3'-methylbenzoate conjugate of 3β-glycyrrhetinic acid, methyl ester (7c) (3.25 g, 4.17 mmole) in tetrahydrofuran (100 mL) and water (20 mL) is treated with 1.0N aqueous lithium hydroxide solution (9 mL) in portions at room temperature over a period of 2 hours. After stirring for an additional 2 hours as above, the reaction is neutralized with IRC50(H+) resin, filtered and evaporated as much as possible (T<35° C.). The final solution is coevaporated with ethyl alcohol (2×20 mL) to remove further traces of tetrahydrofuran, and the remaining aqueous solution diluted with water (15 mL) and lyophilized. The final solid compound is purified by Sephadex LH20 column chromatography; elution using water and 5% ethanol/water as eluents.

Example 8

Preparation of a Compound Containing a β-D-Xylopyranosyl Unit Attached to the 3β-Position of Glycyrrhetinic Acid, Ethyl Ester by a Mercaptoethanol Bridge.

The following compound is prepared:

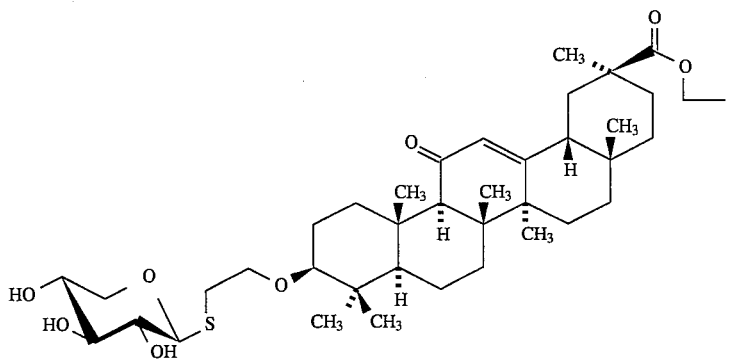

Ethyl, 3β-Hydroxy-11-oxo-18β-olean-12-en-30-oate (8a).

To a solution of glycyrrhetinic acid (25.0 g, 53.23 mmole) in absolute ethanol (300 mL) is added washed, vacuum dried Dowex™50WX12 (H+) resin (10 g) and this mixture is allowed to stir at ambient temperature for 6 hours until t.l.c. indicates that all of the starting acid had been converted to a higher t.l.c. mobile product. The supernatent solution is decanted, and the resin is treated with fresh anhydrous methanol (100 mL). This mixture is allowed to stir as above for 1.5 hours, filtered through a sintered glass Buchner funnel, and the resin is repeatedly washed with methanol (5×20 mL), allowing the resin to equilibrate with the solvent during each wash. The combined methanol filtrates are evaporated to dryness and dried in vacuo to a colorless solid (22.25 g, 84%) which is homogeneous by t.l.c. This material is used without further purification for the production of compound 8b.

Ethyl, 3α-Iodo-11-oxo-18β-olean-12-en-30-oate (8b).

The 3α-iodo derivative of glycyrrhetinic acid, methyl ester is prepared by a method similar to that used above for the preparation of the analogous methyl derivative (see Example 4) [Greenhouse, R., Muchowski, J. M., Can. J. Chem. 59 (1981) 1025–1027]. To a solution of 12.69 g (0.05 mole) of iodine in anhydrous benzene (35 mL) is added a solution of triphenylphosphine (13.12 g, 0.05 mole) in dry benzene (50 mL). After the solution becomes pale, an abundant yellow precipitate of triphenylphosphine diiodide is produced. To this solution is added directly glycyrrhetinic acid, ethyl ester (8a) (4.98 g, 0.01 mole) and this suspension is heated to reflux with stirring for 18 hours. After cooling, the reaction mixture is mixed with ice-water (60 mL) and extracted. The benzene layer is further extracted with water (2×100 mL), dried over anhydrous sodium sulfate, evaporated and dried in vacuo to an off white solid. This residue is triturated with n-pentane (200 ml) and the insoluble triphenylphosphine oxide filtered. After rotary evaporation of the pentane solvent, the product is recrystallized from toluene:acetone.

3β-(2'-Bromoethoxy)-11-oxo-18β-olean-12-en-30-oic Acid, Ethyl Ester (8c).

60% meta-Chloroperbenzoic acid (450 mg), is added in one portion to a stirred solution of the 3α-iodo compound (8b) (3.20 g, 5.27 mmole) and 2-bromoethanol (15 mL, 26.45 g, 40 equivalents) in dry dichloromethane (100 mL). After 4 hours the mixture is made neutral by addition of solid sodium bicarbonate, concentrated in vacuo, and partitioned between ethyl acetate and water. The organic phase is washed with water, dried over anhydrous sodium sulfate and evaporated. The residue is dissolved in dichloromethane and applied to a column of silicagel G (500 g). Elution with diethylether (500 mL) removes nonpolar material and subsequent elution with ethyl acetate (500 mL) gives the partially purified product. Final purification is performed using an HPLC system (eluent=8:1 ethylacetate:hexanes; flow rate=12 mL/min. at 1500 psig.)

3β-(2'-[2,3,4-tri-O-acetyl-1-deoxy-1-thio-β-D-xylopyranosyl] ethoxy)-11-oxo-18β-olean-12-en-30-oic Acid, Ethyl Ester (8d).

The thioglycoside (8d) is prepared by a procedure similar to that used for the synthesis of the rhamnose thioglycoside above (see Example 4) [Cerny, M., Pacak, J., Coll. Czeck. Chem. Commun. 24 (1959) 2566–2569]. To a suspension of the pseudourea (1-deoxy-1-thiouridium-2,3,4-tri-O-acetyl-β-L-xylopyranoside, hydrobromide salt, (prepared from acetobromo-α-D-xylopyranose) 1.87 g, 4.5 mmole) and the bromoethyl ether (8c) (2.72 g, 4.5 mmole) in dry acetone (50 mL) is added an aqueous solution of potassium carbonate (1.24 g, 9 mmole) and sodium hydrosulfite (870 mg, 5.0 mmole). The reaction mixture is allowed to stir at room temperature for 30 minutes, and additional saturated potassium carbonate solution is added to adjust the pH to approximately 9.0. The reaction is allowed to stir for an additional 3 hours, quenched by addition of crushed ice (100 mL) and the product extracted with chloroform (5×50 mL). The combined chloroform layers are dried over anhydrous sodium sulfate, filtered, evaporated and dried in vacuo to a white solid. This crude product is purified by column chromatography to give the final product as a clear foam.

3β-(2'-[1-deoxy-1-thio-β-D-xylopyranosyl]ethoxy)-11-oxo-18β-olean-12-en-30-oic Acid, Ethyl Ester (8e).

A solution of the protected thioxyloside conjugate of 3β-glycyrrhetinic acid, ethyl ester (8d) (2.50 g, 3.06 mmole) is suspended in anhydrous ethanol (500 mL) and cooled to 0° C. (ice-bath) while under an atmosphere of dry nitrogen gas. To this suspension is added freshly prepared sodium ethoxide/ethanol solution (3.5 mL, 1.121 N solution). This reaction is allowed to stir under anhydrous conditions at 0° C. for 2 hours and at room temperature for an additional 18 hours. The reaction is neutralized with washed, dry IRC50(H+) resin (to pH 6), filtered, and the resin washed repeatedly with ethanol. The combined filtrates are evaporated and dried in vacuo to give the title compound.

Example 9

Preparation of a Mixture of Compounds Containing a α-L-Rhamnopyranosyl Unit Attached to the 3α-and 3β-Positions of 4,4-bis(nor-methyl)Glycyrrhetinic Acid by an Ethylene Glycol Bridge.

The following compound is prepared:

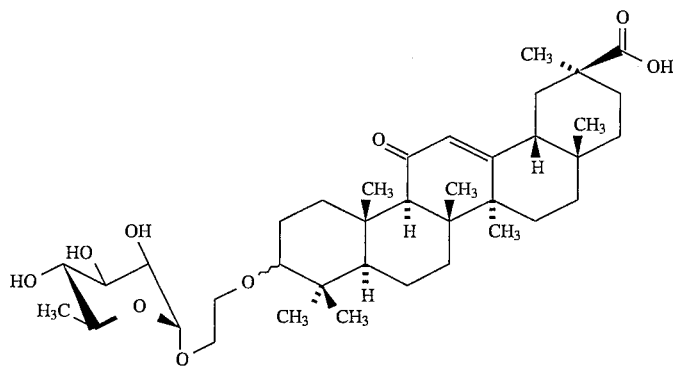

4,4-Desmethyl-3-hydroxy-11-oxo-18β-olean-12-en-30-oic Acid, Methyl Ester (9a).

The 4,4-nor-methyl derivative of glycyrrhetinic acid, methyl ester (9a) is prepared according to the procedure of Baran, et al. [Baran, J. S., Langford, D. D., Liang, C. D., Pitzele, B. S., *J. Med. Chem.* 17(2) (1974) 184–191.] by the reduction of methyl, 4,4-desmethyl-3,11-dioxo-18β-oleane-4,12-diene-30-oate with lithium and ammonia, followed by reduction with lithium tri-tert-butoxyaluminum hydride. The dioxo-diene is in turn prepared by a multistep approach as outlined in the same reference, from glycyrrhetinic acid, methyl ester (3a).

4,4-Desmethyl-3-iodo-11-oxo-18β-olean-12-en-30-oic Acid, Methyl Ester (9b).

The 3α-iodo derivative of 4,4-nor-methyl glycyrrhetinic acid, methyl ester is prepared by a method similar to that used by Greenhouse and Muchowski [Greenhouse, R., Muchowski, J. M., *Can. J. Chem.* 59(1981) 1025–1027] (see Example 1). To a solution of 12.69 g (0.05 mole) of iodine in anhydrous benzene (35 mL) is added a solution of triphenylphosphine (13.12 g, 0.05 mole) in dry benzene (50 mL). After the solution becomes pale, an abundant yellow precipitate of triphenylphosphine diiodide is produced. To this solution is added directly 4,4-nor-methylglycyrrhetinic acid, methyl ester (9a) (4.56 g, 0.01 mole) and this suspension is heated to reflux with stirring for 22 hours. After cooling, the reaction mixture is mixed with ice-water (60 mL) and extracted. The benzene layer is further extracted with water (2×100 mL), dried over anhydrous sodium sulfate, evaporated and dried in vacuo to an off white solid. This residue is triturated with n-pentane (200 ml) and the insoluble triphenylphosphine oxide filtered. After rotary evaporation of the pentane solvent, the product is recrystallized from toluene:acetone.

4,4-Desmethyl-3-(2-hydroxyethoxy)-11-oxo-18β-olean-12-en-30-oic Acid, Methyl Ester (9c).

60% meta-Chloroperbenzoic acid (900 mg), is added in one portion to a stirred solution of the 3-iodo compound (9b) (2.45 g, 4.33 mmole) and ethylene glycol (10 mL, 179 mmole) in dry dichloromethane (25 mL). After 1.5 hours, the reaction mixture is poured into ice-water (30 mL) and the product is extracted with diethylether (3×25 mL). The combined organic phase is washed successively with water and 5% sodium bicarbonate solution, dried over anhydrous sodium sulfate and evaporated in vacuo. The residue is dissolved in dichloromethane and applied to a column of silicagel G (150 g). Elution with diethylether (500 mL) removes nonpolar material and subsequent elution with hexanes:acetone 7:3 (500 mL) gives the partially purified product. Final purification is performed by crystallization from ethyl acetate.

4,4-Desmethyl-3-(2'-O-[2,3,4-tri-O-acetyl-6-deoxy-α-L-mannopyranosylethoxy)-11-oxo-18β-olean-12-en-30-oic Acid, Methyl Ester (9d).

Under anhydrous conditions, a solution of the ethylene glycol ether of 4,4-nor-methylglycyrrhetinic acid, methyl ester (9c) (1.40 g, 2.80 mmole), symcollidine (740 μL, 5.6 mmole), powdered, activated 4A molecular sieves (1 g) and anhydrous silver carbonate (1.55 g, 5.6 mmole) in anhydrous dichloroethane (60 mL) is allowed to stir in the dark under a atmosphere of dry nitrogen gas for 1 hour. Solid 2,3,4-tri-O-acetyl-1-deoxy- 1-bromo α-D-rhamnopyranose (1.98 g, 5.6 mmole) is added to the above solution in portions, with stirring over a period of 15 minutes. The above mixture is allowed to stir at room temperature, as above for 4.5 days, filtered through a Celite™ or diatomaceous earth pad, and the precipitate washed with excess chloroform. The combined filtrates are extracted with water (1×100 mL), ice-cold 1N aqueous HCl (2×100 mL), saturated sodium bicarbonate solution (2×100 mL), 0.1N aqueous sodium thiosulfate solution (1×100 mL) and brine solution (1×100 mL). Each aqueous layer is back-extracted with fresh chloroform (5 mL), and the combined organic layers are dried over anhydrous sodium sulfate, filtered, and evaporated under reduced pressure to a syrup. This crude product is applied to a silicagel G chromatography column (400 g) and eluted by gradient elution using 0–20% ethylacetate in chloroform as eluent. Fractions containing the product are combined and evaporated in vacuo to an off-white powder.

4,4-Desmethyl-3-(2'-O-[6-deoxy-α-L-mannopyranosylethoxy)-11-oxo-18β-olean-12-en-30-oic Acid, Methyl Ester (9e).

A solution of the protected ethyloxy-rhamnoside conjugate of 4,4-nor-methyl glycyrrhetinic acid, methyl ester (9d) (1.50 g, 1.94 mmole) is suspended in anhydrous methanol (200 mL) and cooled to 0° C. (ice-bath) while under an atmosphere of dry nitrogen gas. To this suspension is added freshly prepared sodium methoxide/methanol solution (3.0 mL, 0.911 N solution). This reaction is allowed to stir under anhydrous conditions at 0° C. for 2 hours and at room temperature for 3 hours. The reaction is neutralized with washed, dry IRC50(H+) resin (to pH 6), filtered, and the resin washed repeatedly with methanol. The combined filtrates are evaporated and dried in vacuo to give the title compound.

4,4-Desmethyl-3-(2'-O-[6-deoxy-α-L-mannopyranosylethoxy)-11-oxo-18β-olean-12-en-30-oic Acid (9f).

A solution of the ethoxy-rhamnoside conjugate of 4,4-nor-methyl glycyrrhetinic acid, methyl ester (9e) (1.15 g, 1.78 mmole) in tetrahydrofuran (50 mL) and water (10 mL) is treated with 1.0 N aqueous lithium hydroxide solution (6.5 mL) in portions at room temperature over a period of 2 hours. After stirring for an additional 2 hours as above, the reaction is neutralized with IRC50(H+) resin, filtered and evaporated as much as possible (T<35° C.). The final solution is coevaporated with ethyl alcohol (2×20 mL) to remove further traces of tetrahydrofuran, and the residual aqueous solution diluted with water (15 mL) and lyophilized. The final solid compound is purified by Sephadex LH20 column chromatography; elution using water and 5% ethanol/water as eluents.

Example 10

Anti-Inflammatory Effects

Using the arachidonic acid (AA), murine skin inflammation model, described by Harris, R. R. et al. (*Skin Pharmacal* 1990; 3:29–40) the antiinflammatory activity of 3-0-fucoside-18-β glycyrrhetinic acid was tested. For comparison, glycyrrhetinic acid was also tested. All compounds were dissolved at 100mg/ml in either methanol or chloroform (glycyrrhetinic acid). 10 µl of each compound was applied to the ear. AA was applied alone, or followed immediately with 3-0-fucoside-18-β glycyrrhetinic acid or glycyrrhetinic acid. 90 minutes later a 6mm disk of each ear was removed, and weighed. It was observed that the % maximal inflammatory response caused by AA alone was reduced by about 60% for both 3-0-fucoside-18-β and glycyrrhetinic acid. The results were the average of 6 experiments.

The instant invention is shown and described herein in what is considered to be the most practical, and preferred embodiments. It is recognized, however, that departures may be made therefrom which are within the scope of the invention, and that obvious modifications will occur to one skilled in the art upon reading this disclosure.

What is claimed is:

1. A derivative of a triterpenoid acid having the structural formula (I) :

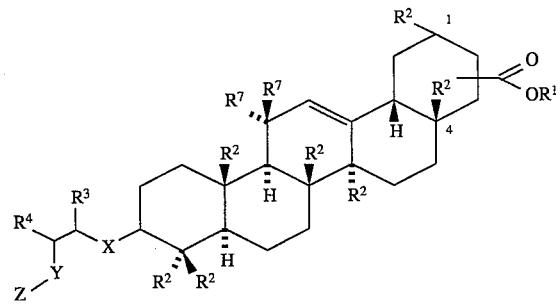

$R^1$ is H or lower alkyl containing 1 to 4 carbon atoms;

$R^2$ is $CH_2OR^1$ or $CH_3$;

$R^3$ and $R^4$ are each independently H or alkyl containing 1 to 6 carbon atoms or $R^3$ and $R^4$, taken together, form a deoxy sugar in its D or L form or a six-membered ring optionally containing a heteroatom selected from the group consisting of O, S, $NR^1$, wherein said six-membered ring may further be substituted by one or more substituents selected from the group consisting of $CH_2OR^1$, $OR^1$, $OOCR^1$, $NR^1_2$, $NHCOR^1$, $SR^1$, $COOR^1$;

X is O, S, $NR^1$;

Y is O, S, $NR^1$; and

Z is $CHR^5(CHOR^1)_nCHR^6$ or an aromatic ring substituted with up to 3-OH, wherein $R^5$ and $R^6$ are each independently H, lower alkyl or taken together to form a five or six-membered ring optionally containing a heteroatom selected from the group of O, S, and $NR^1$;

said five or six-membered ring optionally substituented with a substituent selected from group consisting of $CH_2OR^1$, $OR^1$, $OOCR^1$, $NR^1_2$, $NHCOR^1$, $SR^1$, and $COOR^1$;

with the proviso that if $R^3$ and $R^4$, taken together, provide a hexose substituent, Z cannot represent a hexose substituent;

n is 2 or 3

$R^7$ is —H, or together both $R^7$ groups are =O, or =$NR^1$;

with the proviso that if E ring substitution is in the 1-position, $R^3$ and $R^4$ taken together cannot provide a hexose substituent; and stereoisomers of a compound of formula (I).

2. The triterpenoid derivative of claim 1, wherein $R^1$ is hydrogen, $R^2$ is $CH_3$; $R^3$ and $R^4$ are each independently hydrogen or an alkyl containing 1, 2 and 6 carbon atoms; Y is O; Z is $CHR^5$ $(CHOR^1)_n$ $CHR^6$ wherein $R^5$ and $R^6$ are each independently hydrogen or a lower alkyl containing 1 to 4 carbon atoms; n is 2 or 3; and $R^7$ is =O.

3. The triterpenoid acid derivative of claim 2, wherein $R^3$ and $R^4$ are each hydrogen and n is 2.

4. A pharmaceutical composition, comprising:

a pharmaceutically acceptable excipient; and a therapeutically effective amount of a derivative of a triterpenoid acid having the structural formula (I):

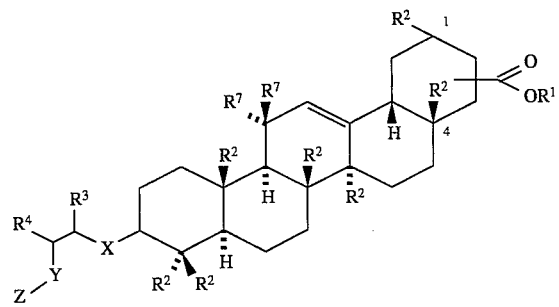

$R^1$ is H or lower alkyl containing 1 to 4 carbon atoms;

$R^2$ is $CH_2OR^1$ or $CH_3$;

$R^3$ and $R^4$ are each independently H or alkyl containing 1 to 6 carbon atoms or $R^3$ and $R^4$, taken together, form a deoxy sugar in its D or L form or a six-membered ring optionally containing a heteroatom selected from the group consisting of O, S, $NR^1$, wherein said six-membered ring may further be substituted by one or more substituents selected from the group consisting of $CH_2OR^1$, $OR^1$, $OOCR^1$, $NR^1_2$, $NHCOR^1$, $SR^1$, $COOR^1$;

X is O, S, $NR^1$;

Y is O, S, $NR^1$; and

Z i s $CHR^5(CHOR^1)_nCHR^6$ or an aromatic ring substituted with up to 3-OH, wherein $R^5$ and $R^6$ are each independently H, lower alkyl or taken together to form a five or six-membered ring optionally containing a heteroatom selected from the group of O, S, and $NR^1$;

said five or six-membered ring optionally substituted with a substituent selected from group consisting of $CH_2OR^1$, $OR^1$, $OOCR^1$, $NR^1_2$, $NHCOR^1$, $SR^1$, and $COOR^1$;

with the proviso that if $R^3$ and $R^4$, taken together, provide a hexose substituent, Z cannot represent a hexose substituent;

n is 2 or 3

$R^7$ is —H, or together both $R^7$ groups are =O, or =$NR^1$;

with the proviso that if E ring substitution is in the 1-position, $R^3$ and $R^4$ taken together cannot provide a hexose substituent; and stereoisomers of a compound of formula (I).

5. The pharmaceutical composition of claim 4, wherein $R^1$ is hydrogen, $R^2$ is $CH_3$; $R^3$ and $R^4$ are each independently hydrogen or an alkyl containing 1, 2 and 6 carbon atoms; Y is O; Z is $CHR^5$ $(CHOR^1)_n$ $CHR^6$ wherein $R^5$ and $R^6$ are each independently hydrogen or a lower alkyl containing 1 to 4 carbon atoms; n is 2 or 3; and $R^7$ is =O.

6. An acetate test material for determining the presence of a selectin in a sample, comprising:

a substrate, the surface of which has bound thereto a compound having the structural formula (I):

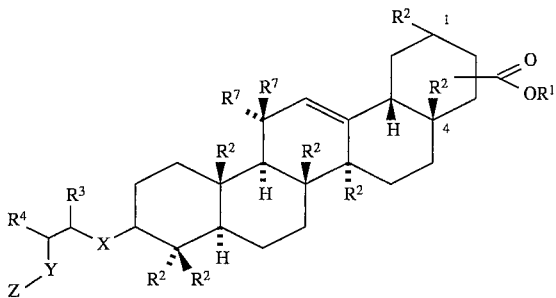

$R^1$ is H or lower alkyl containing 1 to 4 carbon atoms;

$R^2$ is $CH_2OR^1$ or $CH_3$;

$R^3$ and $R^4$ are each independently H or alkyl containing 1 to 6 carbon atoms or $R^3$ and $R^4$, taken together, form a deoxy sugar in its D or L form or a six-membered ring optionally containing a heteroatom selected from the group consisting of O, S, $NR^1$, wherein said six-membered ring may further be substituted by one or more substituents selected from the group consisting of $CH_2OR^1$, $OR^1$, $OOCR^1$, $NR^1_2$, $NHCOR^1$, $SR^1$, $COOR^1$;

X is O, S, $NR^1$;

Y is O, S, $NR^1$; and

Z is $CHR^5$ $(CHOR^1)_n$ $CHR^6$ or an aromatic ring substituted with up to 3-OH, wherein $R^5$ and $R^6$ are each independently H, lower alkyl or taken together to form a five or six-membered ring optionally containing a heteroatom selected from the group of O, S, and $NR^1$;

said five or six-membered ring optionally substituted with a substituent selected from group consisting of $CH_2OR^1$, $OR^1$, $OOCR^1$, $NR^1_2$, $NHCOR^1$, $SR^1$, and $COOR^1$;

with the proviso that if $R^3$ and $R^4$, taken together, provide a hexose substituent, Z cannot represent a hexose substituent;

n is 2 or 3

$R^7$ is —H, or together both $R^7$ groups are =O, or =$NR^1$;

with the proviso that if E ring substitution is in the 1-position, $R^3$ and $R^4$ taken together cannot provide a hexose substituent; and stereoisomers of a compound of formula (I).

7. A method of treating inflammation, comprising the steps of:

administering to a patient in need thereof a therapeutically acceptable amount of the composition of claim 4; and allowing the composition to bind to selectins in the patient and thereby treat inflammation.

* * * * *